US008742283B2

(12) United States Patent  
Morrisroe

(10) Patent No.: US 8,742,283 B2  
(45) Date of Patent: Jun. 3, 2014

(54) INDUCTION DEVICE

(75) Inventor: Peter J Morrisroe, New Milford, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 13/602,267

(22) Filed: Sep. 3, 2012

(65) Prior Publication Data

US 2012/0325783 A1     Dec. 27, 2012

Related U.S. Application Data

(63) Continuation of application No. 12/343,034, filed on Dec. 23, 2008, now Pat. No. 8,263,897, which is a continuation of application No. 11/218,912, filed on Sep. 2, 2005, now Pat. No. 7,511,246, which is a continuation-in-part of application No. 10/730,779, filed on Dec. 9, 2003, now Pat. No. 7,106,438.

(60) Provisional application No. 60/432,963, filed on Dec. 12, 2002.

(51) Int. Cl.
    *B23K 10/00*         (2006.01)

(52) U.S. Cl.
    USPC ............. 219/121.48; 219/121.52; 315/111.51

(58) Field of Classification Search
    CPC ...................................................... B23K 10/00
    USPC .......................... 219/121.48, 121.52, 121.43; 315/111.51; 356/316; 250/288
    See application file for complete search history.

(56) References Cited

U.S. PATENT DOCUMENTS

| | | | |
|---|---|---|---|
| 1,958,406 A | 5/1934 | Darrah |
| 2,708,341 A | 5/1955 | Zucrow |
| 2,833,371 A | 5/1958 | Honma |
| 2,847,899 A | 8/1958 | Walsh |
| 3,004,137 A | 10/1961 | Karlovitz |
| 3,052,614 A | 9/1962 | Herold |
| 3,224,485 A | 12/1965 | Blomgren |
| 3,248,513 A | 4/1966 | Sunnen |
| 3,264,508 A | 8/1966 | Lai |
| 3,408,283 A | 10/1968 | Chopra |
| 3,416,870 A | 12/1968 | Wright |
| 3,428,401 A | 2/1969 | Buzza |

(Continued)

FOREIGN PATENT DOCUMENTS

| | | |
|---|---|---|
| EP | 281158 | 9/1988 |
| EP | 602764 | 6/1994 |

(Continued)

OTHER PUBLICATIONS

Official Action for Australian Patent Application No. 2006284864.

(Continued)

*Primary Examiner* — Mark Paschall  
(74) *Attorney, Agent, or Firm* — Rhodes IP PLC; Christopher R Rhodes

(57) ABSTRACT

A device for sustaining a plasma in a torch is provided. In certain examples, the device comprises a first electrode configured to couple to a power source and constructed and arranged to provide a loop current along a radial plane of the torch. In some examples, the radial plane of the torch is substantially perpendicular to a longitudinal axis of the torch.

14 Claims, 20 Drawing Sheets

(56) References Cited

U.S. PATENT DOCUMENTS

| | | | |
|---|---|---|---|
| 3,492,074 A | 1/1970 | Rendina | |
| 3,619,061 A | 11/1971 | Mitchell | |
| 3,668,066 A | 6/1972 | Hendel | |
| 3,958,883 A | 5/1976 | Turner | |
| 4,004,117 A * | 1/1977 | Amsler | 218/123 |
| 4,118,618 A | 10/1978 | Gauthier | |
| 4,256,404 A | 3/1981 | Walker | |
| 4,263,089 A | 4/1981 | Keller | |
| 4,293,220 A | 10/1981 | Denton | |
| 4,300,834 A | 11/1981 | Demers | |
| 4,362,936 A | 12/1982 | Hofmann | |
| 4,419,575 A | 12/1983 | Lakatos | |
| 4,482,246 A | 11/1984 | Meyer | |
| 4,540,884 A * | 9/1985 | Stafford et al. | 250/282 |
| 4,575,609 A | 3/1986 | Fassel | |
| 4,578,583 A | 3/1986 | Ciammaichella | |
| 4,578,589 A | 3/1986 | Aitken | |
| 4,629,940 A * | 12/1986 | Gagne et al. | 315/111.51 |
| 4,640,627 A | 2/1987 | Tracy | |
| 4,736,101 A | 4/1988 | Syka | |
| 4,766,287 A | 8/1988 | Morrisroe | |
| 4,782,235 A | 11/1988 | Lejeune | |
| 4,795,880 A | 1/1989 | Hayes | |
| 4,798,464 A | 1/1989 | Boostrom | |
| 4,812,166 A | 3/1989 | Saiki | |
| 4,818,916 A | 4/1989 | Morrisroe | |
| 4,886,359 A | 12/1989 | Berndt | |
| 4,897,282 A | 1/1990 | Kniseley | |
| 4,906,900 A | 3/1990 | Asmussen | |
| 4,955,717 A | 9/1990 | Henderson | |
| 5,024,725 A | 6/1991 | Chen | |
| 5,217,362 A | 6/1993 | Thompson | |
| 5,259,254 A | 11/1993 | Zhu | |
| 5,308,977 A | 5/1994 | Oishi | |
| 5,334,834 A | 8/1994 | Ito | |
| 5,356,674 A | 10/1994 | Henne | |
| 5,438,194 A | 8/1995 | Koudijs | |
| 5,468,955 A | 11/1995 | Chen | |
| 5,526,110 A | 6/1996 | Braymen | |
| 5,534,998 A | 7/1996 | Eastgate | |
| 5,597,467 A | 1/1997 | Zhu | |
| 5,640,841 A | 6/1997 | Crosby | |
| 5,648,701 A | 7/1997 | Hooke | |
| 5,680,014 A | 10/1997 | Miyamoto | |
| 5,818,581 A * | 10/1998 | Kurosawa et al. | 356/316 |
| 5,916,455 A | 6/1999 | Kumagai | |
| 5,958,258 A | 9/1999 | Ishihara | |
| 5,975,011 A | 11/1999 | Ohkusa | |
| 5,994,697 A | 11/1999 | Kato | |
| 6,033,481 A | 3/2000 | Yokogawa | |
| 6,041,735 A | 3/2000 | Murzin | |
| 6,080,271 A * | 6/2000 | Fujii | 156/345.48 |
| 6,227,465 B1 | 5/2001 | Kelly | |
| 6,236,012 B1 | 5/2001 | Carre | |
| 6,248,998 B1 | 6/2001 | Okumoto | |
| 6,329,757 B1 | 12/2001 | Morrisroe | |
| 6,453,660 B1 | 9/2002 | Johnson | |
| 6,541,766 B2 | 4/2003 | Kato | |
| 6,614,021 B1 | 9/2003 | Kalinitchenko | |
| 6,617,794 B2 | 9/2003 | Barnes | |
| 6,621,078 B2 | 9/2003 | Taniguchi | |
| 6,627,877 B1 | 9/2003 | Davis | |
| 6,639,227 B1 | 10/2003 | Glavish | |
| 6,809,312 B1 | 10/2004 | Park | |
| 6,899,787 B2 | 5/2005 | Nakano | |
| 7,106,438 B2 | 9/2006 | Morrisroe | |
| 7,114,337 B2 | 10/2006 | Cazalens | |
| 7,119,330 B2 | 10/2006 | Kalinitchenko | |
| 7,276,688 B2 | 10/2007 | Weiss | |
| 7,323,655 B2 | 1/2008 | Kim | |
| 7,511,246 B2 * | 3/2009 | Morrisroe | 219/121.48 |
| 7,622,693 B2 | 11/2009 | Foret | |
| 7,737,397 B2 | 6/2010 | Morrisroe | |
| 7,742,167 B2 | 6/2010 | Morrisroe | |
| 7,880,147 B2 | 2/2011 | Morrisroe | |
| 2002/0125425 A1 | 9/2002 | Kato | |
| 2003/0184234 A1 | 10/2003 | Hsu | |
| 2004/0001295 A1 | 1/2004 | Kumar | |
| 2004/0124779 A1 | 7/2004 | Howald | |
| 2004/0169855 A1 | 9/2004 | Morrisroe | |
| 2004/0173579 A1 | 9/2004 | Carr | |
| 2004/0219737 A1 | 11/2004 | Quon | |
| 2005/0082471 A1 | 4/2005 | Kalinitchenko | |
| 2006/0136158 A1 | 6/2006 | Goldberg | |
| 2006/0163468 A1 | 7/2006 | Wells | |
| 2006/0285108 A1 | 12/2006 | Morrisroe | |
| 2006/0286492 A1 | 12/2006 | Morrisroe | |
| 2008/0017794 A1 | 1/2008 | Verbeck | |
| 2008/0173810 A1 | 7/2008 | Morrisroe | |

FOREIGN PATENT DOCUMENTS

| | | |
|---|---|---|
| EP | 0673186 | 9/1995 |
| EP | 1891407 | 2/2008 |
| JP | 56000911 | 1/1981 |
| JP | 59207828 | 11/1984 |
| JP | 62273047 | 11/1987 |
| JP | 1109648 | 4/1989 |
| JP | 1124951 | 5/1989 |
| JP | 2001265500 | 10/1989 |
| JP | 4008873 | 1/1992 |
| JP | 06027083 | 2/1994 |
| JP | 6283484 | 10/1994 |
| JP | 7057893 | 3/1995 |
| JP | 7153420 | 6/1995 |
| JP | 7211489 | 8/1995 |
| JP | 07307199 | 11/1995 |
| JP | 11258163 | 9/1999 |
| JP | 2001-183297 | 7/2001 |
| JP | 2002343599 | 11/2002 |
| JP | 2003168594 | 6/2003 |
| JP | 2003168595 | 6/2003 |
| JP | 2003194273 | 7/2003 |
| JP | 2003215042 | 7/2003 |
| JP | 05-288682 | 10/2005 |
| JP | 2006-516325 | 6/2006 |
| JP | 2005018688 | 7/2007 |
| JP | 10-022096 | 1/2010 |
| WO | 8806834 | 9/1988 |
| WO | 9638856 | 12/1996 |
| WO | 2004055493 | 7/2004 |

OTHER PUBLICATIONS

First official action for JP2008529236.
International Search Report/Written Opinion for PCT/US06/008687.
Eden et al. J. Phys. D: Apply. Phys. 36: 2869-2877, Dec. 2003.
Kikuchi et al. J. Phys D: Appl. Phys. 37: 1537-1543, Jun. 2004.
Boswell et al. IEEE Transaction on Plasma Sciences, 25: Dec. 1997.
First official action for CN200680006366.2.
First official action for AU2006223254.
First official action for JP500981/2008.
International Search Report/Written Opinion for PCT/US2009/000278 dated Oct. 6, 2009.
EP Communication for EP06748915.8.
First Official Action for CN 200680021600.X.
International Search Report/Written Opinion for PCT/US2006/0232777.
Second Official Action for CN200680021600.X.
Eden et al. J. Phys. D: Appl. Phys. 36: 2869-2877, Dec. 2003.
Kikuchi et al. J. Phys. D: Appl. Phys 37: 1537-1543, Jun. 2004.
Boswell et al. IEEE Transactions on Plasma Science, 25: Dec. 1997.
EP Communication for EP06784915.8.
Second Official Action for CN 200680021600.X.
IPRP for PCT/US2006/223277 dated Dec. 2007.
First official action for Australian Patent Application No. 2006259381.
International Search/Written Opinion for IPCT/US2006/223277 dated Dec. 2007.
Official Action for AU 2003293514.

* cited by examiner

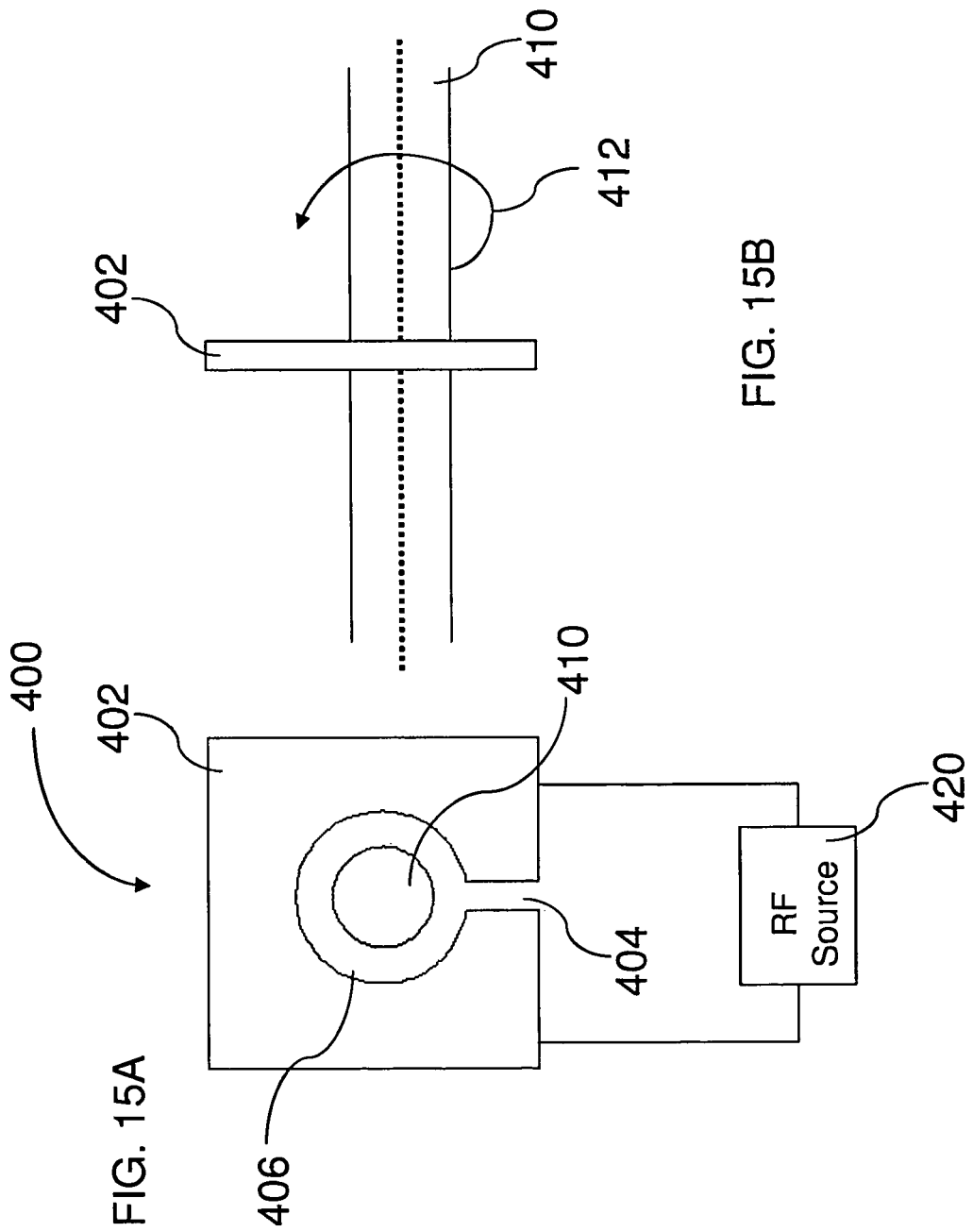

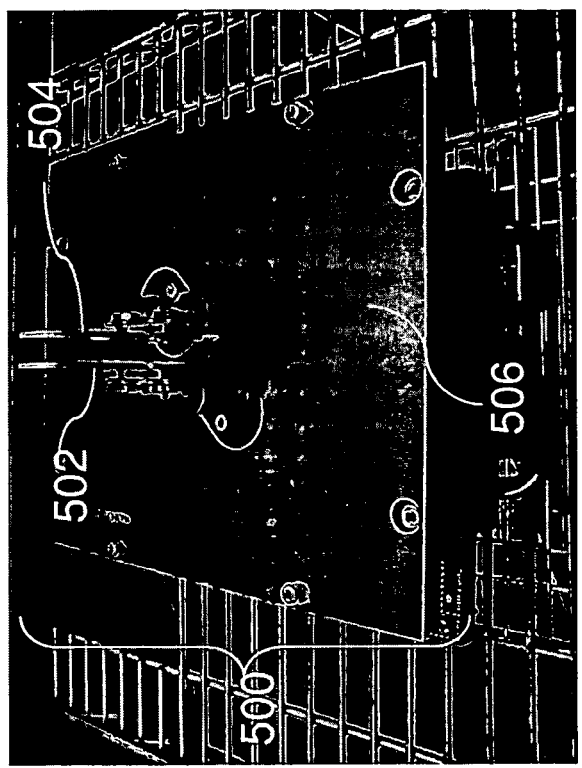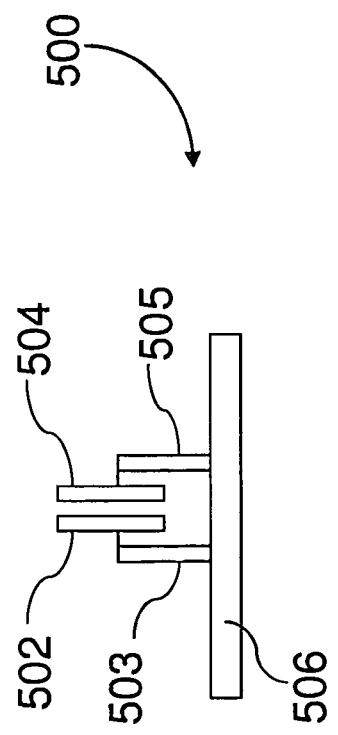
FIG. 16A
FIG. 16B

INDUCTION DEVICE

PRIORITY APPLICATION

This application is a continuation of U.S. patent application Ser. No. 12/343,034, filed on Dec. 23, 2008, which is a continuation of U.S. patent application Ser. No. 11/218,912 (now U.S. Pat. No. 7,511,246) filed on Sep. 2, 2005, which is a continuation-in-part of U.S. patent application Ser. No. 10/730,779 (now U.S. Pat. No. 7,106,438) filed on Dec. 9, 2003, which claimed priority to U.S. Provisional Application No. 60/432,963 filed on Dec. 12, 2002, the entire disclosure of each of which is hereby incorporated herein by reference for all purposes.

FIELD OF THE TECHNOLOGY

Certain examples relate to devices and methods for use in generating a plasma and to methods and apparatus for analyzing a sample introduced into in a plasma generated by such devices.

BACKGROUND

Many inductively coupled plasma optical emission spectroscopy (ICP-OES) systems, inductively coupled plasma atomic absorption spectroscopy (ICP-AAS) systems, and inductively coupled plasma mass spectroscopy (ICP-MS) systems use a solenoid receptive of an RF electrical current for forming a plasma. However, the induced current generated by the magnetic field is skewed and non-homogeneous over the length of the interior of the solenoid due to the helical configuration of the solenoid. This non-homogeneity results in a variable temperature distribution within the plasma, which can affect sample excitation and the trajectory of ions in the plasma. In addition, the solenoid is a single element, which lacks flexibility in controlling the associated induced current formed by the magnetic field and the plasma/sample excitation.

SUMMARY

In accordance with a first aspect, a device for use in generating a plasma is provided. In certain examples, a device for generating a plasma in a torch having a longitudinal axis along which a flow of gas is introduced during operation of the torch and having a radial plane substantially perpendicular to the longitudinal axis of the torch is disclosed. In certain some, the device comprises a first electrode configured to couple to a power source and constructed and arranged to provide a loop current along the radial plane of the torch is provided. In certain examples, the device further includes a second electrode configured to couple to a power source and constructed and arranged to provide a loop current along the radial plane of the torch. In some examples, each of the first and second electrodes comprises a plate comprising a symmetrical inner cross-section, e.g., a circular inner cross-section. In certain examples, at least one spacer separates the first and second electrode. In other examples, the first electrode is configured to sustain a symmetrical plasma, or a substantially symmetrical plasma, in the torch, as described herein. In certain examples, the first electrode, the second electrode or both may be in electrical communication with a radio frequency source configured to provide RF power to one or more of the electrodes. In some examples, the first electrode and the second electrode each have their own radio frequency source. In certain examples, the first electrode, the second electrode or both, are in electrical communication with a grounding plate. The device may be configured for use in an inductively coupled plasma optical emission spectrometer, an inductively coupled plasma atomic absorption spectrometer, an inductively coupled plasma mass spectrometer or other suitable instrument.

In accordance with another aspect, a device for generating a plasma in a torch having a longitudinal axis along which a low of gas is introduced during operation of the torch and having a radial plane substantially perpendicular to the longitudinal axis of the torch is disclosed. In certain examples, the device comprises means for providing a loop current along the radial plane of the torch. In some examples, the means may be an electrode or an equivalent structure that can provide a radio frequency current along the radial plane of the torch. In certain examples, the means may be a plate electrode, as described herein.

In accordance with an additional aspect, a method of sustaining a plasma in a torch having a longitudinal axis and having a radial plane substantially perpendicular to the longitudinal axis of the torch is provided. In certain examples, the method includes providing a gas flow along the longitudinal axis of the torch, igniting the gas flow in the torch, and providing a loop current along the radial plane to sustain a plasma in the torch. In some examples the method further includes configuring the plasma to be a substantially symmetrical plasma.

In accordance with another aspect, a substantially symmetrical plasma is disclosed. In certain examples, the substantially symmetrical plasma may be produced by igniting a gas flow in a torch and providing a loop current along a radial plane substantially perpendicular to a longitudinal axis of the torch to sustain the substantially symmetrical plasma.

Additional aspects and examples will be recognized by the person of ordinary skill in the art, given the benefit of this disclosure, and certain aspects and examples are described in more detail below.

BRIEF DESCRIPTION OF THE FIGURES

Certain examples are described below with reference to the accompanying figures in which:

FIGS. 15A and 15B show a torch and an induction device configured to generate a current loop, in accordance with certain examples;

FIGS. 16A and 16B are induction devices, in accordance with certain examples;

It will be recognized by the person of ordinary skill in the art, given the benefit of this disclosure, that the exemplary induction devices and other devices shown in the figures may not be to scale. Certain features or dimensions of the induction devices, the torches and the like may have been enlarged, reduced or distorted relative to other features to facilitate a better understanding of aspects and examples disclosed herein.

DETAILED DESCRIPTION

Certain examples are described below to illustrate some of the many applications and uses of the induction device technology disclosed herein. These and other uses will be readily selected by the person of ordinary skill in the art, given the benefit of this disclosure. Unless otherwise clear from the context, like numerals refer to similar structures in different figures.

In accordance with certain examples, a device for generating a symmetrical or substantially symmetrical plasma is disclosed. As used herein, "symmetrical plasma" refers to a plasma having a symmetrical temperature profile, for a selected radial plane, extending radially from the center of the plasma. For example, a radial slice of a plasma would have a life-saver shaped torus discharge associated with that radial slice. For any given radius from the center of the torus, the temperature is fairly uniform for any given angle of measurement around the center for that radius. As used herein, "substantially symmetrical plasma" refers to a plasma that has a similar temperature profile, for a selected radial plane, extending radially from the center of the plasma, but the temperature profile may vary up to about 5% for any given radius from the center of the torus discharge. Use of a symmetrical plasma, or a substantially symmetrical plasma, may provide significant benefits including, but not limited to, less carbon build-up in the torch, less torch maintenance, an ion trajectory that is substantially parallel to the axial direction, i.e., the longitudinal axis, of the torch, more efficient sample transfer into the center of the plasma, and may allow for reduced amounts of cooling gas or using no cooling gas at all. Also as used herein, "substantially perpendicular" refers to being perpendicular to within about 5 degrees. It will be recognized by the person of ordinary skill in the art, given the benefit of this disclosure, that a torch includes numerous radial planes perpendicular to the longitudinal axis of a torch, and that reference herein to a loop current along a radial plane does not imply or suggest positioning of the loop current in any one specific position along the longitudinal axis of the torch.

Figure 1:
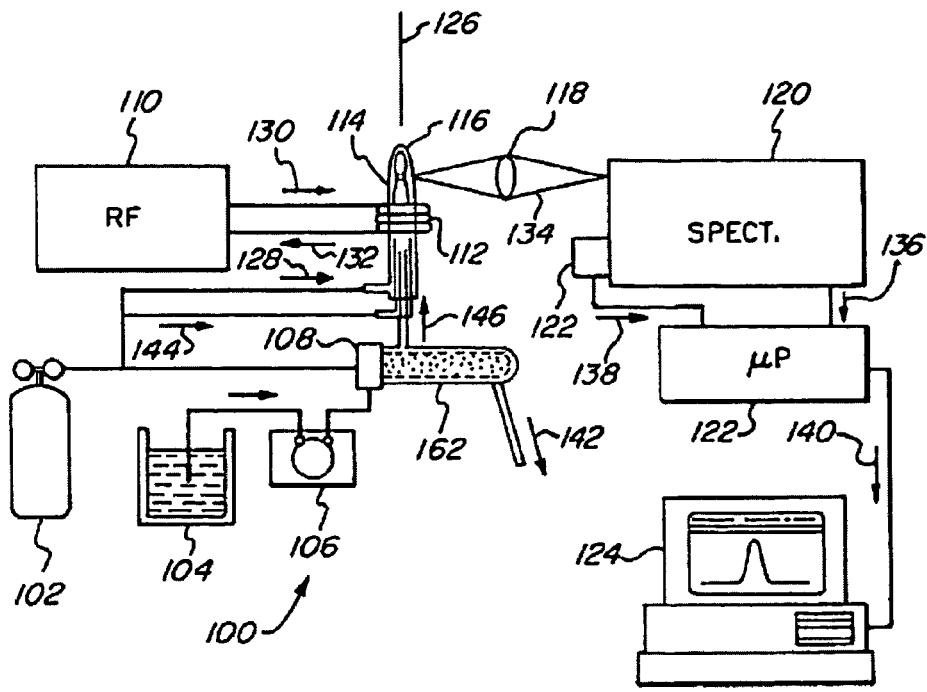
FIG. 1 is schematic diagram of an inductively coupled plasma-optical emission spectrometer (ICP-OES), in accordance with certain examples.

Referring now to FIG. 1, a schematic diagram of an exemplary inductively coupled plasma-optical emission spectrometer (ICP-OES) 100 is shown. In certain examples, the ICP-OES 100 generally comprises a system for directing a carrier gas 102 to a torch 114 where the carrier gas 102 is ionized to form a hot plasma 116 (e.g., 5,000-10,000K or greater). In some examples, the plasma 116 comprises a preheating zone 190, an induction zone 192, an initial radiation zone 194, an analytic zone 196 and a plasma tail 198 (see FIG. 3). An atomized sample 104 may be directed to the plasma 116 through a pump 106, nebulizer 108 and spray chamber 162. In the illustrative configuration shown in FIG. 1, a RF power source 110 provides RF power to the plasma 116 by way of an induction device 112. In plasma 116, excited sample atoms 104 may emit light 134 as the excited atoms decay to a lower state. The emitted light 134 may be collected by collection optics 118 and directed to a spectrometer 120 where it is spectrally resolved. A detector 122 may be operative to detect the spectrally resolved light 134 and provide a signal 138, 140 to a microprocessor 122 and computer network 124 for analysis. In examples where the species do not emit light, an inductively coupled atomic absorption spectrometer may be used to provide light to the atomized species and a detector may be used to detect light absorption by the atomized species. Illustrative atomic absorption spectrometers are available from PerkinElmer, Inc. and exemplary atomic absorption spectrometers are described, for example, in commonly owned U.S. Provisional No. 60/661,095 entitled "Plasmas and Devices Using Them" and filed on Mar. 11, 2005, the entire disclosure of which is hereby incorporated herein by reference for all purposes.

In FIG. 1, the plasma 116 is shown as being viewed from a direction at a right angle to the longitudinal axis of the plasma 116, i.e., viewed radially or viewed along the radial axis. However, it will be understood by the person of ordinary skill in the art, given the benefit of this disclosure, that the viewing of the plasma 116 may also be performed from a direction along the longitudinal axis 126 of the plasma 116, i.e., viewed axially. Detection of light emissions in the axial direction can provide significant signal-to-noise benefits.

Figure 2:
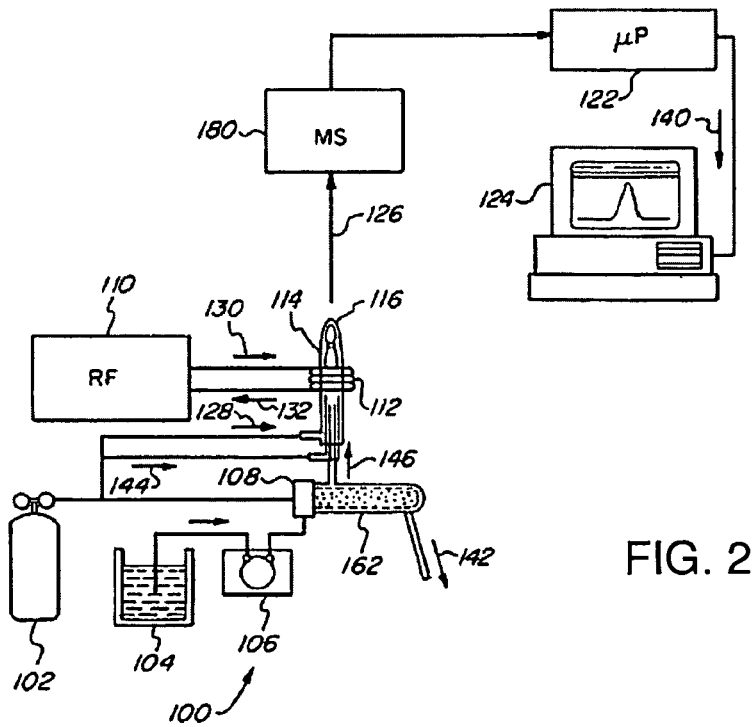
FIG. 2 is schematic diagram of an inductively coupled plasma-mass spectrometer (ICP-MS), in accordance with certain examples.

It will also be understood by the person or ordinary skill in the art, given the benefit of this disclosure, that the inductively coupled plasma may also be used with a mass spectrometer, (MS) 180 such as a quadrupole mass analyzer in an inductively coupled plasma-mass spectrometer (ICP-MS) 100 as seen in FIG. 2. The RF power source 110 operates generally in the range of about 1 to about 500 MHz, particularly 20-50 MHz, e.g., 27-40 MHz and powers of about 100 Watts to about 10 kiloWatts are supplied to the electrodes to generate the magnetic field. Illustrative mass spectrometers are commercially available from PerkinElmer, Inc. and exemplary mass spectrometers are described, for example, in commonly owned U.S. Provisional No. 60/661,095 entitled "Plasmas and Devices Using Them" and filed on Mar. 11, 2005.

Figure 3:
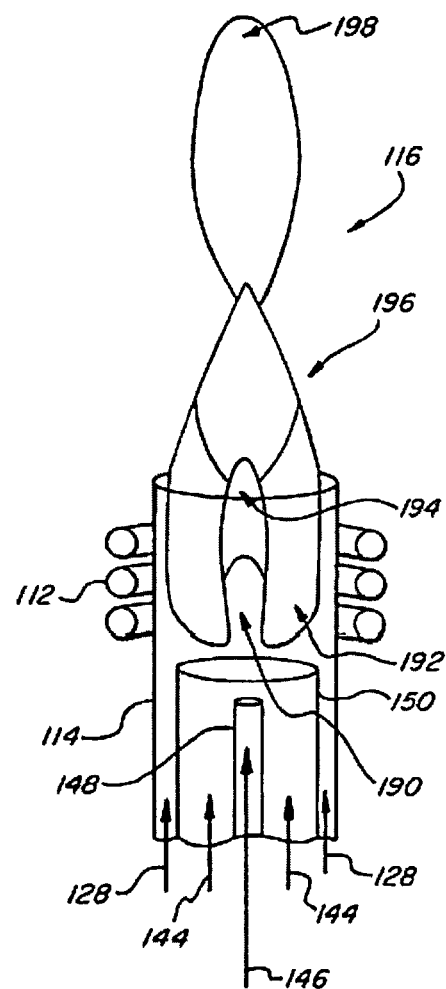
FIG. 3 is a diagram of an ICP torch and a plasma, in accordance with certain examples.

FIG. 3 shows a more detailed schematic of the plasma 116 of FIGS. 1 and 2. The torch 114 includes three concentric tubes 114, 150, and 148. The innermost tube 148, provides atomized flow 146 of the sample into the plasma 116. The middle tube 150, provides auxiliary gas flow 144 to the plasma 116. The outermost tube 114, provides carrier gas flow 128 for sustaining the plasma. The carrier gas flow 128 may be directed to the plasma 116 in a laminar flow about the middle tube 150. The auxiliary gas flow 144 may be directed to the plasma 116 within the middle tube 150 and the atomized sample flow 146 may be directed to the plasma 116 from the spray chamber 162 along the innermost tube 148. The RF current 130, 132 in the load coil 112 may form a magnetic field within the load coil 112 so as to confine the plasma 116 therein.

Figure 4:
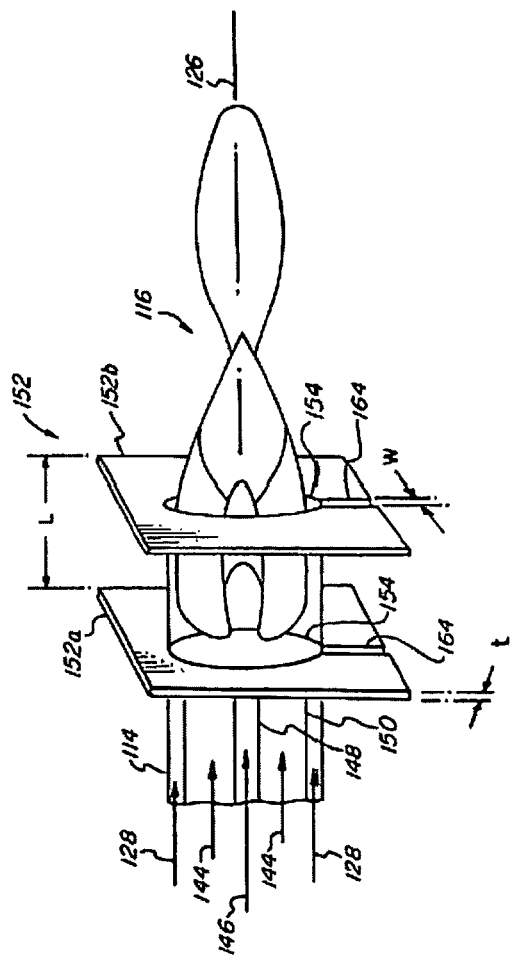
FIG. 4 is a side view of two electrodes, an ICP torch and a plasma, in accordance with certain examples.

The plasmas shown in FIGS. 1-3, and shown in certain other figures described herein, can be generated using numerous different electrode configurations. FIGS. 4-11 show various configurations of an electrode 152, 156, 158. In FIG. 4, the electrode 152 comprises two substantially parallel plates 152a, 152b positioned at a distance 'L' from one another. In certain examples, the substantially parallel plates have a width of about 20 mm to about 200 mm, e.g., about 40 mm, and a length of about 30 mm to about 90 mm, e.g., about 70 mm. Each of the parallel plates 152a, 152b includes an aperture 154 through which the torch 114 may be positioned such that the torch 114, the innermost tube 148, the middle tube 150 and the aperture 154 are aligned along an axis 126. The exact dimensions and shapes of the aperture may vary and may be any suitable dimensions and shapes that can accept a torch. For example, the aperture may be generally circular and have a diameter of about 10 mm to about 60 mm, may be square or rectangular shaped and have dimensions of about 20 mm to about 60 mm wide by about 20 mm to about 100 mm long, may be triangular, oval, ovoid, or other suitable geometries. If a small diameter torch is used such as a "low flow" torch then the diameter of the aperture can be reduced proportionally to accommodate the torch. In certain examples, the aperture may be sized such that it is about 0-50% or typically about 3% larger than the torch, whereas in other examples, the torch may contact the plates, e.g., some portion of the torch may contact a surface of a plate, without any substantial operational problems. The substantially parallel plates 152a, 152b have a thickness of 't.' In some examples, each of plates 152a and 152b have the same thickness, whereas in other examples plates 152a and 152b may have different thicknesses. In certain examples, the thickness of the plates is from about 0.025 mm (e.g., such as a metallized plating on an insulator, an example of this would be copper, nickel, silver, or gold plating on a ceramic substrate) to about 20 mm, more particularly, about 0.5 mm to about 5 mm, or any particular thickness within these exemplary ranges. The aperture 154 of the electrode 152 may also include a slot 164, of width 'w' such that the aperture 154 is in communication with its surroundings. The width of the slot may vary from about 0.5 mm to about 20 mm, more particularly, about 1 mm, to about 3 mm, e.g., about 1 mm to about 2 mm.

In accordance with certain examples, the electrodes may be constructed from the same or different materials. In certain examples, the electrodes may be constructed from conductive materials such as, for example, aluminum, gold, copper, brass, steel, stainless steel, conductive ceramics and mixtures and alloys thereof. In other examples the electrodes may be constructed from non-conductive materials that include a plating or coating of one or more conductive materials. In some examples, the electrodes may be constructed from materials capable of withstanding high temperatures and resisting melting when exposed to the high circulating currents required to generate the plasma. These and other suitable materials for constructing the electrodes will be readily selected by the person of ordinary skill in the art, given the benefit of this disclosure.

Figure 5:
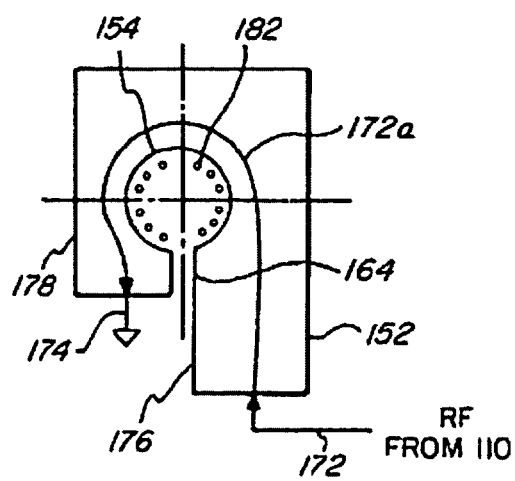
FIG. 5 is a front view of a first electrode for sustaining a plasma, the electrode including an aperture, in accordance with certain examples.
Figure 12:
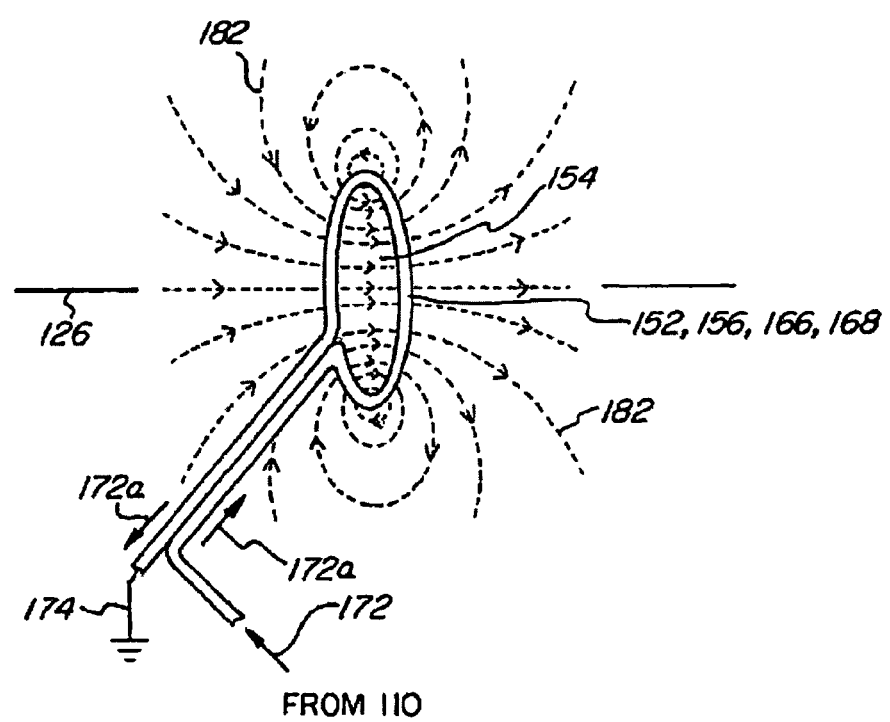
FIG. 12 is a perspective view of a magnetic field generated from a loop current, in accordance with certain examples.

Referring to FIGS. 4 and 5, the electrode 152 may be generally comprised of a square or rectangular planar shape, though it may be a wire as seen in FIG. 12. In certain examples, the RF current supplied to the planar electrode creates a planar loop current 172a, which generates a toroidal magnetic field 182 through the aperture 154 (see FIG. 12). The planar current loop may be substantially parallel to a radial plane, which is substantially perpendicular to the longitudinal axis of the torch. The toroidal magnetic field may be operative to generate and sustain a plasma within a torch, such as torch 114 shown in FIG. 3. In a typical plasma, argon gas may be introduced into the torch at flow rates of about 15-20 Liters per minute. A plasma may be generated using a spark or an arc to ignite the argon gas. The toroidal magnetic field causes argon atoms and ions to collide, which results in a superheated environment, e.g., about 5,000-10,000 K or higher, that forms the plasma.

Figure 7:
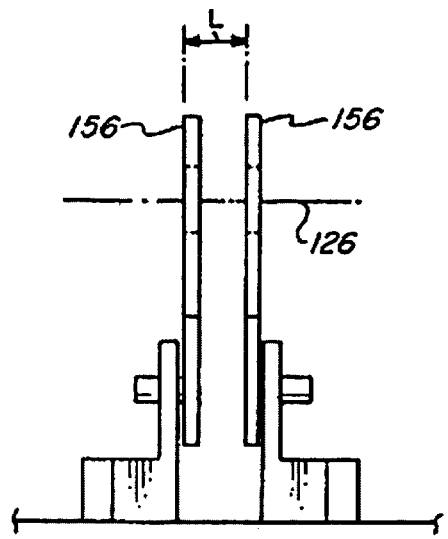
FIG. 7 is a side view of the electrode of FIG. 6, in accordance with certain examples.
Figure 6:
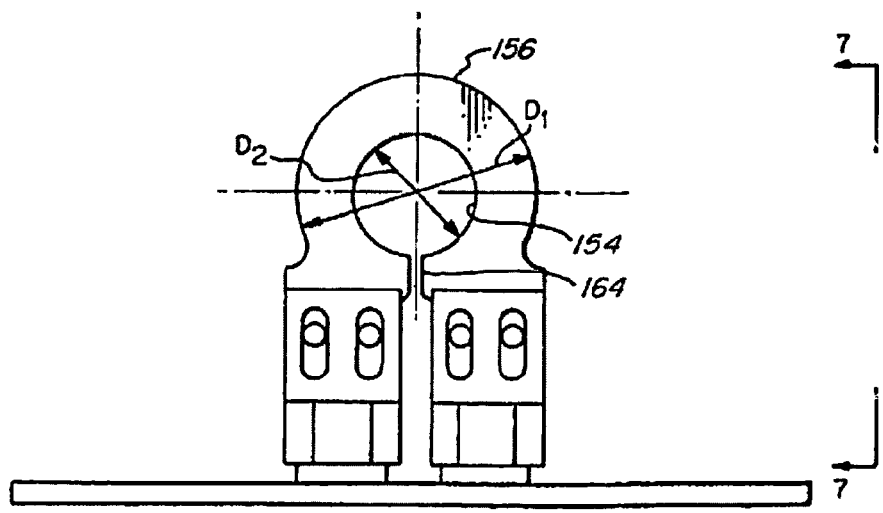
FIG. 6 is a front view of a second electrode for sustaining a plasma, the electrode including an aperture, in accordance with certain examples.
Figure 8:
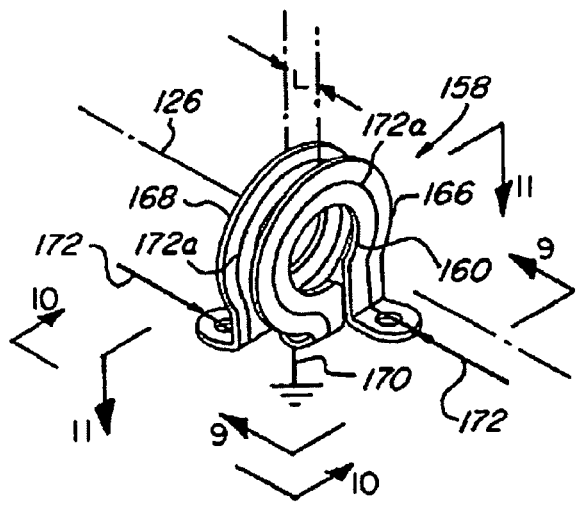
FIG. 8 is a perspective view of a unitary electrode, in accordance with certain examples.
Figure 9:
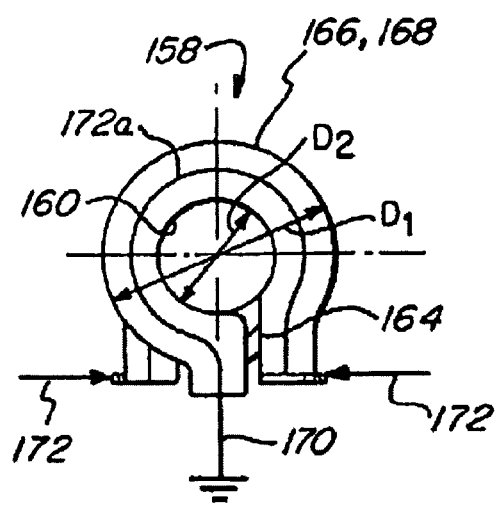
FIG. 9 is a front view of the electrode of FIG. 8, in accordance with certain examples.
Figure 10:
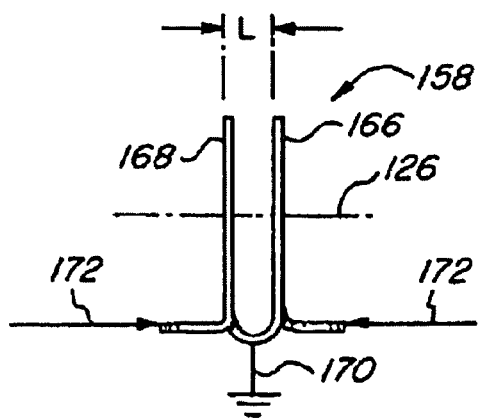
FIG. 10 is a side view of the electrode of FIG. 8, in accordance with certain examples.
Figure 11:
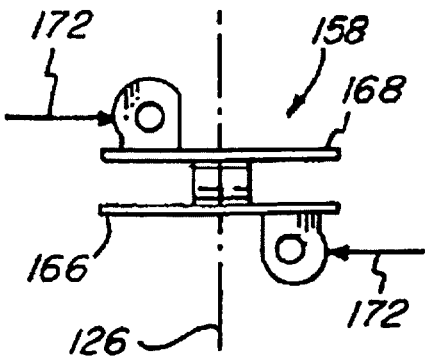
FIG. 11 is a top view of the electrode of FIG. 8, in accordance with certain examples.

Referring now to FIGS. 6 and 7, the electrode 156 may be of a rounded nature having an outside diameter of $D_1$ and inside aperture diameter of $D_2$. In some examples, the outside diameter ranges from about 10 mm to about 20 cm, more particularly about 25 mm to about 10 cm, e.g., about 30 mm to about 50 mm, and the inside diameter ranges from about 10 mm to about 15 cm, more particularly, from about 5 mm to about 5 cm, e.g., about 20 mm to about 24 mm. In certain examples, electrodes 152, 156 of FIGS. 4-7 may be distinct elements which are supplied independently with RF electrical current 172 and typically of opposite polarity (though opposite polarity is not required for operation). In other examples, electrodes 152, 156 of FIGS. 4-7 may be elements in electrical communication and may each be suitably designed to provide the desired polarity to generate a magnetic field.

In accordance with certain examples, one part 176 of the electrode 152 may be supplied with the RF power while a second part 178 of the electrode 152 may be tied to a ground 174. In some examples, the electrode may be grounded to the instrument chassis, whereas in other examples, the electrode may be mounted and grounded to a grounding plate, which itself may be grounded in a suitable manner During arc ignition of the plasma 116, if the ignition arc makes contact with electrode 152, any unwanted electric currents set up in the electrode 152 may be directed to the ground point 174 and not through to the RF power supply 110. The RF power and frequency supplied to each electrode 152 may be independently controlled and varied for optimum performance. For instance, each electrode 152 may be operated at a different frequency in order to optimize the plasma emission and excitation. In addition, one electrode (or both electrodes) may be operated in a continuous power mode while the other electrode can be modulated (e.g., pulsed or gated). In certain examples, the distance, 'L', between the electrodes 152 may be adjusted since the electrodes 152 are not connected to one another, which can result in adjustment of the power distribution within the plasma 116. Yet further, the diameter, $D_2$ of the aperture 154 may be independently adjusted in order to adjust the coupling characteristics between the RF power supply 110 and the plasma 116.

In accordance with certain examples, spacers may be placed between some portion of the electrodes to control the distance between the electrodes. In certain examples, the spacers are constructed using the same materials used to construct the electrodes. In some examples, the spacers are made from a material having substantially the same coefficient of thermal expansion as the electrode material so that as the electrode expands and contracts with different temperatures, the spacer expands and contracts at about the same rate. In some examples, the spacers are stainless steel washers, brash washers, copper washers or washers made from other suitable conductive materials. In certain examples, the spacers are washers that are sized suitably to receive a bolt or nut that connects the electrodes. By using one or more spacers, the distance between the electrodes may be easily reproduced and/or altered. It will be within the ability of the person of ordinary skill in the art, given the benefit of this disclosure, to select suitable materials and shapes for spacers for use with the electrodes disclosed herein.

Referring now to FIGS. 8-11, induction device 158 is shown as including two electrodes 166, 168 connected to a common electrical ground 170. Induction coil 158 may be configured as a helical coil with electrodes 166 and 168 being in electrical communication with each other. When RF current 172 is supplied to induction device 158, loop currents 172a are generated, which creates a toroidal magnetic field. Loop currents 172a are substantially parallel to the planar surfaces of electrodes 166 and 168 and would be substantially perpendicular to the longitudinal axis of the torch. Induction coil 158 may be grounded at common electrical ground 170 (see FIG. 10) to prevent unwanted arcing, which can result in melting of electrodes 166 and 168. In certain examples, electrodes 166 and 168 are spaced a distance L from each other (see FIGS. 8 and 10). The exact distance between electrodes 166 and 168 can vary and exemplary distances include, but are not limited to, about 1 mm to about 5 cm, more particularly about 2 mm to about 2 cm, e.g., about 5 mm to about 15 mm. In certain examples, electrodes 166 and 168 are arranged substantially perpendicular to a mounting surface. In other examples, electrodes 166 and 168 may be tilted at an angle so that the axial dimension of the torch and the radial dimension of the electrodes are substantially perpendicular. In some examples, each of electrodes 166 and 168 may be angled in the same direction, whereas in other examples, electrodes 166 and 168 may be angled in opposite directions. The person of ordinary skill in the art, given the benefit of this disclosure, will be able to select suitable configurations and angles for the electrodes of the illustrative induction devices disclosed herein.

Figure 13:
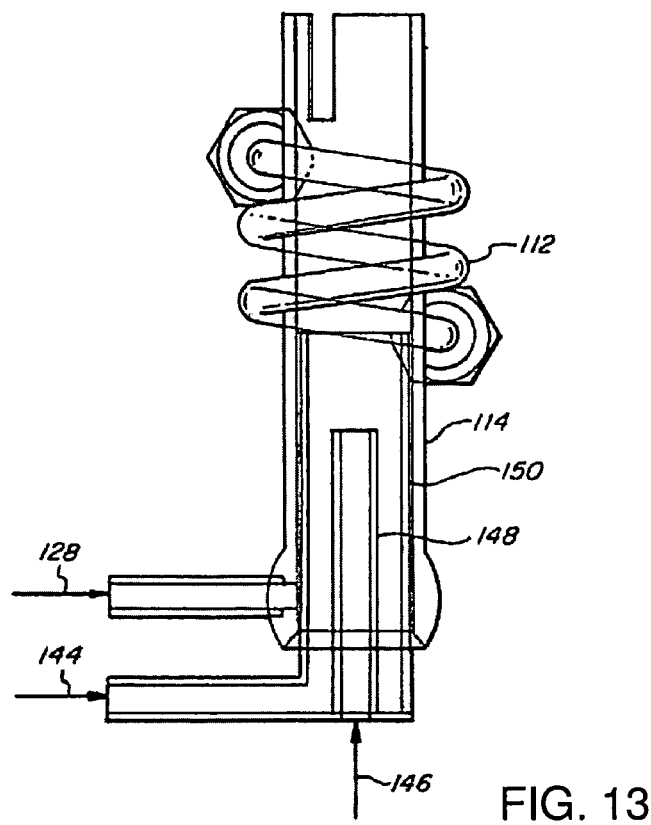
FIG. 13 is a diagram of an ICP torch showing the helical nature of a solenoid, in accordance with certain examples.

In accordance with certain examples, an exemplary configuration of an induction device surrounding a torch is shown in FIG. 13. Induction device 112 may surround concentric fluid conduits 114, 150 and 148. Carrier gas flow 128 may be introduced into the torch to provide gas for generation of the plasma using induction device 112. Auxiliary gas flow 144 may be introduced into concentric tube 150 to provide gas for controlling the plasma position relative to the injector 148. Sample flow 146 may enter aerosol conduit 148 where it is sprayed into the plasma generated by induction device 112. The exact flow rates of the various gas species may vary. For example, the carrier gas is typically introduced at a flow rate of about 10 L/min to about 20 L/min, e.g., about 15-16 L/minute. The auxiliary gas is typically introduced at a flow rate of about 0 L/min to about 2 L/minute. The sample can be introduced at a suitable flow rate to provide desolvation and/or atomization of the sample. In some examples, the sample is introduced at a flow rate of about 0.1 L/minute to about 2 L/minute. Additional flow rates for the carrier gas, auxiliary gas and sample will be readily selected by the person of ordinary skill in the art, given the benefit of this disclosure.

Figure 14:
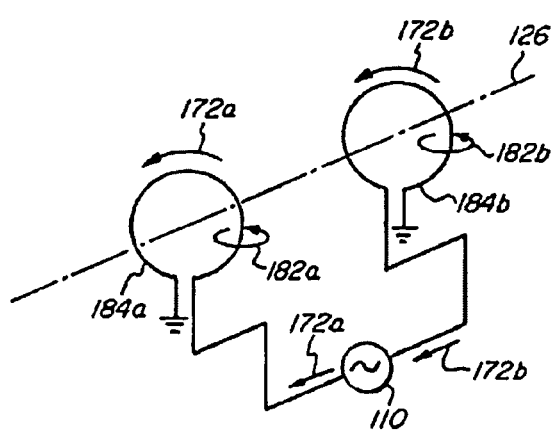
FIG. 14 is a diagram of a plurality of loop currents driven by a single RF power source during alternating half cycles of a sinusoidally alternating current, in accordance with certain examples.

Referring now to FIG. 14, a plurality of loop currents 184a, 184b are shown generated from a single RF electric current source 110. For clarity of illustration, the electrodes have been omitted from FIG. 14. The loop currents 184a, 184b are generated by applying a current of opposite polarities to apposing electrodes. The loop currents 184a, 184b may be oriented with respect to one another in a suitable manner such that the alternating electric current 172a in a first loop current 184a flows in the same direction as that of the alternating electric current 172b in a second loop current 184b during alternating half cycles of a sinusoidally alternating current. This configuration allows for the plurality of loop currents 184a, 184b to be driven from a single power source 110 so as to generate magnetic fields 182a, 182b having the same spatial orientation. An example of this can be seen in FIGS. 17 and 18, where diagonally apposing legs of each coil 1002 and 1004 are driven from a single RF source located directly below, and the remaining two legs, also diagonally apposing, are commonly connected to a grounded plate 1006. The plane of the loop currents 184a, 184b is also substantially perpendicular to the longitudinal axis 126 of the torch and is substantially parallel to a radial plane of the torch. In certain examples, the device includes two or more electrodes constructed and arranged to generate a magnetic field to sustain a symmetrical or substantially symmetrical plasma. Certain exemplary electrodes are discussed above in reference to FIGS. 1-14 and other exemplary electrodes are discussed below.

In accordance with certain examples, a device for generating a plasma comprising a first electrode constructed and arranged to provide a first loop current along a radial plane that is substantially perpendicular to a longitudinal axis of a torch is disclosed. Referring to FIGS. 15A and 15B, device 400 includes electrode 402, which has a slot 404 and an aperture 406 for receiving a torch 410. The electrode 402 has a circular inner cross-section that is substantially symmetrical. In certain examples, the diameter of the inner cross-section is about 10 mm to about 60 mm, more particularly about 20 mm to about 30 mm, e.g., about 20 mm to about 23 mm. In some examples, the diameter of the inner cross-section is selected such that about 1 mm of distance separates the outer surface of the torch 410 from the inner portion of the electrode 402. The electrode 402 may be positioned such that it is substantially perpendicular to the longitudinal axis (shown in FIG. 15B as a dotted line) of the torch 410. The slot 404 of the electrode 402 may be configured such that the current provided to electrode 402 will take the form of a loop, such as a loop current 412 shown in FIG. 15B. In some examples, the loop current 412 is substantially perpendicular to the longitudinal axis of the torch 410, e.g., the plane of the loop current is substantially perpendicular to the longitudinal axis of the torch 410. Use of a substantially perpendicular loop current may generate and/or sustain a plasma that has a more symmetrical temperature distribution, for a selected radial plane, than plasmas generated using helical load coils. In certain examples, a symmetrical plasma, or substantially symmetrical plasma, is sustained using an electrode, such as the electrode 402, positioned substantially perpendicular to the longitudinal axis of the torch 410. In certain examples, the selected overall shape of the electrode may vary. For example and as shown in FIG. 15A, electrode 402 is configured with an overall rectangular shape. However, other suitable shapes, such as circles, triangles, rings, ellipses, toroids and the like may also be used. The first electrode may be mounted to a grounding plate as described herein.

In certain examples, a second electrode similar to the electrode 402 in FIG. 15A may also be constructed and arranged parallel to a radial plane, which is substantially perpendicular to a longitudinal axis of a torch 410. In other examples, the plane of the second loop current may be substantially parallel to the plane of the first loop current. In some examples, the first and second loop currents may flow in the same direction, whereas in other examples the first and second loop currents may flow in an opposite direction. In examples where more than one electrode is used, a single RF source, such as RF source 420 shown in FIG. 15A, may provide RF power to each of the first and second electrodes, or separate RF sources may provide RF power to the first and second electrodes. In some examples, spacers are used to separate the first and second electrodes. In examples where a single RF source is used to provide RF power to the first and second electrodes and where spacers are used, the spacers may be made of a conductive material, e.g., copper, brass, gold and the like. In examples where separate RF sources are used to provide RF power to the first and second electrodes and where spacers are used, the spacers may be made of a non-conductive material, e.g., glass, plastics, etc., to prevent current flow from the first electrode to the second electrode.

In accordance with certain examples, the first electrode, the second electrode or both may be grounded to a grounding plate. For example, and referring now to FIGS. 16A and 16B, induction device 500 may include a first electrode 502 and a second electrode 504 each mounted to a grounding plate 506. In the example shown in FIGS. 16A and 16B, the electrodes 502 and 504 may be mounted to the grounding plate 506 using supports 503 and 505, respectively. In certain examples, the diagonally apposing legs of each electrode 502 and 504 may be driven from a single RF source located directly below, the remaining two legs, also diagonally apposing, may be commonly connected to a grounding plate 506, and all components may be electrically connected through the four identical mounts typically identified as 503 and 505. The supports 503 and 505 may provide electrical communication between the electrodes 502 and 504 and the grounding plate 506 such that during arc ignition of the plasma, if an ignition arc makes contact with the electrodes 502, 504, any unwanted electric currents set up in the electrodes 502, 504 may be directed to the grounding plate 506 and not passed through to the RF power supply (not shown) in electrical communication with the electrodes 502 and 504. Use of the electrodes 502 and 504 with the grounding plate 506 may provide a more symmetrical plasma, which can improve detection limits of certain species (as discussed in more detail in the examples herein), than plasmas generated using helical load coils. For example, using existing helical load coils there may exist areas of the plasma that have a reduced temperature and are inefficient at desolvation and atomization due to the plasmas tendency to follow the helix of the load coil resulting in a non-uniform plasma discharge. Using examples of the induction devices disclosed herein, a plasma having a more symmetrical temperature distribution, for a selected radial plane, is generated which can provide for more even desolvation and atomization, which results in improved performance, extended torch life, and less carbon buildup when used with organics.

In certain examples, an induction device as disclosed herein may be operated at much lower powers than conventional helical load coils. For example, a power of about 800 Watts to about 1250 Watts, e.g., about 900 Watts to about 1050 Watts, may be used with an induction device disclosed herein to sustain a plasma suitable for use, for example, in instruments for chemical analysis. For comparative purposes only, a typical conventional helical load coil uses about 1450 Watts of power or more to sustain a plasma suitable for chemical analysis. In some examples, an induction device provided herein is configured to use about 10-20% less power than a helical load coil.

In accordance with certain examples, the exact thickness of the electrode and the grounding plate can vary depending, for example, on the intended use of the device, the desired shape of the plasma, etc. In certain examples, the electrode is about 0.05-10 mm thick, more particularly, about 1-7 mm, thick, e.g., about 1, 2, 3, 4, 5, or 6 mm thick or any dimensions between these illustrative thicknesses. Similarly, the exact dimensions and thickness of the grounding plate may vary. For example, the grounding plate may be from about 5 mm to about 500 mm wide to about 5 mm to about 500 mm long, or it could be as large as the whole instrument chassis itself, and may have a thickness from about 0.025 mm thick to about 20 mm thick. It will be within the ability of the person of ordinary skill in the art, given the benefit of this disclosure, to select suitable electrode and grounding plate dimensions and thicknesses to provide a desired plasma shape.

Figure 16C:
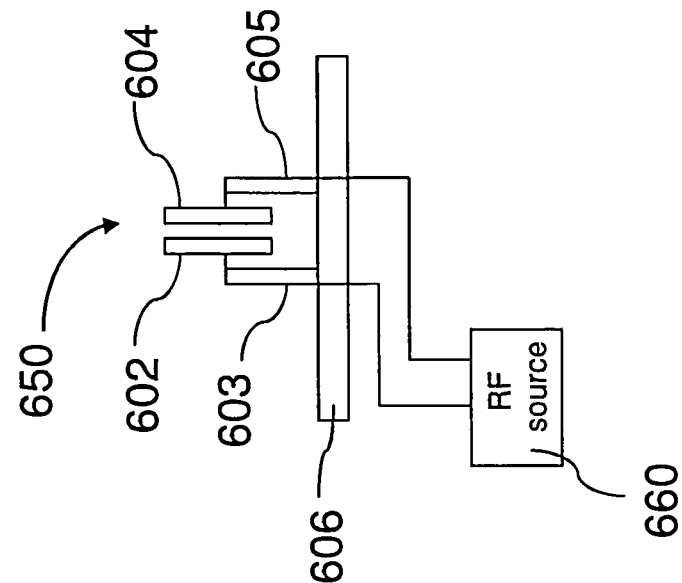
FIGS. 16C and 16D are induction devices, in accordance with certain examples.
Figure 16D:
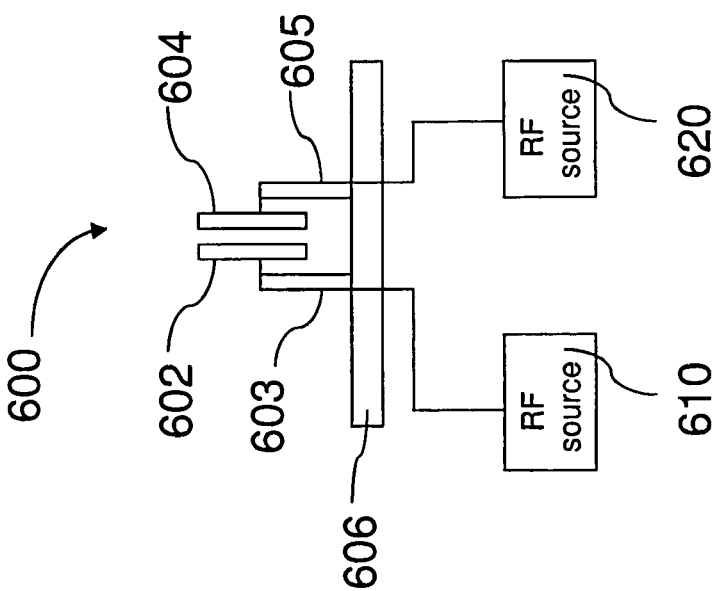

In accordance with certain examples, each electrode of an induction device may be individually tuned or controlled. Referring to FIG. 16C, an induction device 600 includes electrodes 602 and 604 in electrical communication with a grounding plate 606 through supports 603 and 605, respectively. The grounding plate 606 may be configured to prevent unwanted arcing, which can result in melting of the electrodes 602, 604. In certain configurations, the grounding plate 606 may itself be grounded to the instrument chassis. An RF source 610 may be configured to provide a current to the electrode 602, and an RF source 620 may be configured to provide a current to the electrode 604. The current supplied to the electrodes 602 and 604 may be the same or may be different. The current may also be altered or changed during operation of the plasma to change the shape and/or temperature of the plasma. In other examples, a single RF source may be configured to provide current to both electrodes 602, 604. For example and referring to FIG. 16D, an induction device 650 includes electrodes 602 and 604 in electrical communication with a grounding plate 606 through supports 603 and 605, respectively. An RF source 660 may be configured to provide a current to each of the electrodes 602 and 604. Even though a single RF source may be used to provide current to the electrodes 602 and 604, the current supplied to each electrode may or may not be the same. For example, suitable electronic circuitry may be implemented to supply one of the electrodes with a different current. The person of ordinary skill in the art, given the benefit of this disclosure, will be able to design suitable induction devices using one or more RF sources.

In accordance with certain examples, a device for sustaining a plasma in a torch having a longitudinal axis along which a flow of gas is introduced during operation of the torch and having a radial plane substantially perpendicular to the longitudinal axis of the torch is provided. In certain examples, the device includes means for providing a loop current along a radial plane of the torch. Suitable means include, but are not limited to, any one or more of the electrodes disclosed herein or other suitable devices that can provide loop currents along a radial plane.

In accordance with certain examples, a method of sustaining a plasma in a torch having a longitudinal axis and having a radial plane substantially perpendicular to the longitudinal axis of the torch is disclosed. In certain examples, the method includes providing a gas flow along the longitudinal axis of the torch, igniting the gas flow in the torch, and providing a loop current along the radial plane to sustain a plasma in the torch. The loop current may be provided using any one or more of the electrodes disclosed herein or other suitable electrode configurations that may provide a loop current along a radial plane. In certain examples, the plasma which is sustained using the method described herein is a substantially symmetrical plasma.

In accordance with certain examples, a signal from the plasma may be monitored between the two or more of the electrodes of the induction device. In some examples, radial detection of optical emission of excited species between the electrodes, or above the electrodes, may be performed using standard optical detectors. In other examples, axial detection may be used to monitor the signal from the plasma or species in the plasma.

Suitable electronic components for providing current to the electrodes will be readily selected by the person of ordinary skill in the art, given the benefit of this disclosure. For example, illustrative RF sources and oscillators may be found in U.S. Pat. No. 6,329,757, the entire disclosure of which is hereby incorporated herein by reference for all purposes.

Certain specific examples are discussed in more detail below to further illustrate aspects and examples of the technology.

Example 1

Plate Induction Coil

Figure 17:
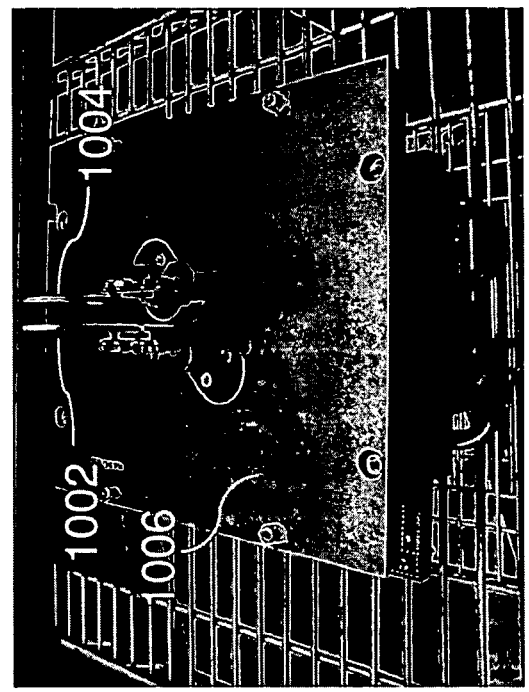
FIG. 17 is an axial view of an induction device, in accordance with certain examples.
Figure 18:
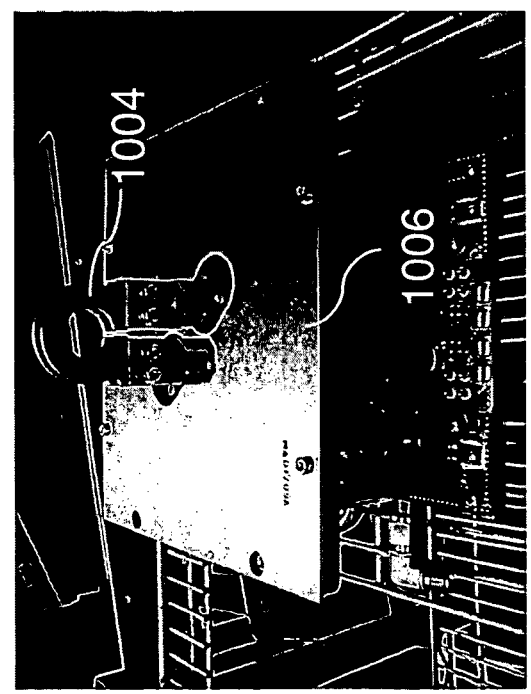
FIG. 18 is a radial view of the induction device of FIG. 17, in accordance with certain examples.
Figure 20:
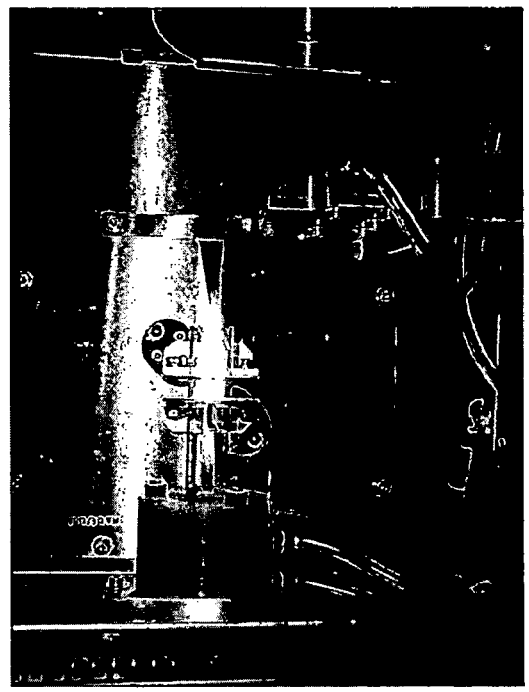
FIG. 20 is a view of a plasma generated using the induction device of FIGS. 17 and 18, in accordance with certain examples.
Figure 19:
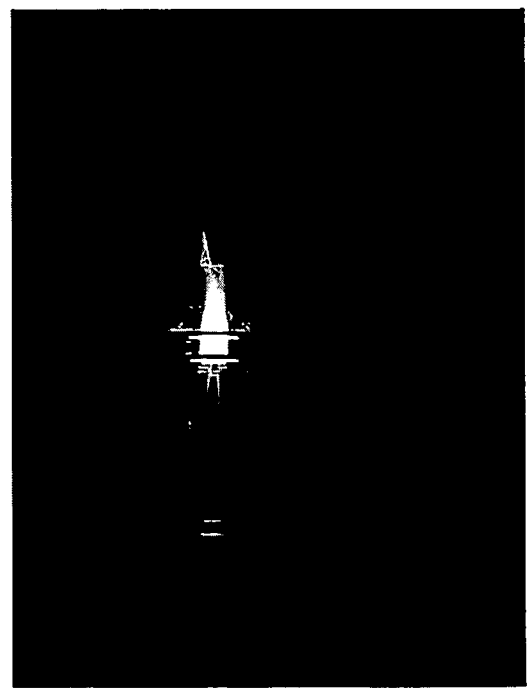
FIG. 19 is a view of a plasma generated using the induction device of FIGS. 17 and 18, viewed through a piece of welding glass, in accordance with certain examples.

An induction device 1000 was assembled with two electrodes 1002 and 1004, each of which were grounded to grounding plate 1006 (see FIGS. 17 and 18). The electrodes 1002 and 1004 were each 2 mm thick plates machined out of 50-52 sheet aluminum. A modified face plate was installed and evaluated on Optima 2000 and Optima 4000 instruments, available from PerkinElmer, Inc. This face plate, as shown in FIGS. 17 and 18, included the replacement of the helical load coil with the grounding plate 1006, inductors 1002 and 1004 and mounts. Very minor modifications were needed to the faceplate to include clearance holes where needed for the bolts securing mounting blocks. No functional changes were made to the generator. The modified instrument was tested to ensure that it met all of the instrument specifications at a flow rate of about 15 L/minute (see plasma shown in FIG. 19 (viewed through welding glass) and FIG. 20). The temperature of the oscillator heat sink, for the same input power, was cooler than when the helical load coil was used. A lower oscillator heat sink temperature indicated more power was getting to the plasma. The plasma could also be maintained at a lower power (about 1250 Watts) than the power used with a conventional helical load coil (about 1450 Watts). In addition, when the instrument was operated at 1450 Watts, the induction device was better able to handle the sample loading than the helical coil at the same power setting.

Example 2

Symmetrical Plasma Discharge

Figure 22:
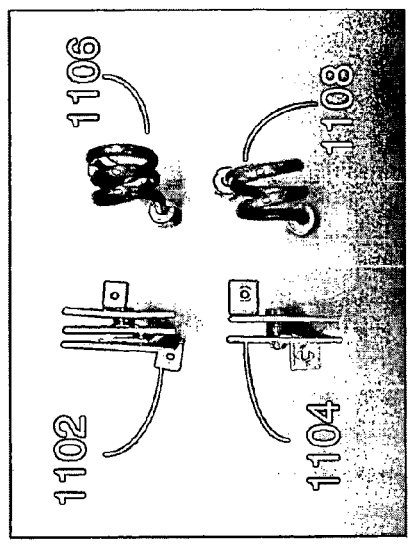
FIG. 22 shows a radial view of induction devices with plate electrodes and a radial view of standard helical load coils, in accordance with certain examples.
Figure 21:
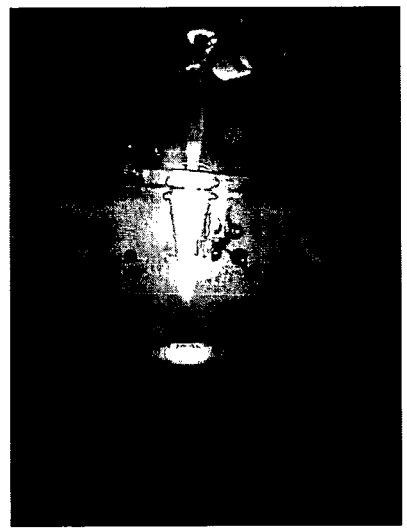
FIG. 21 is an example of a symmetrical plasma generated using an induction device with plate electrodes, in accordance with certain examples.
Figure 23:
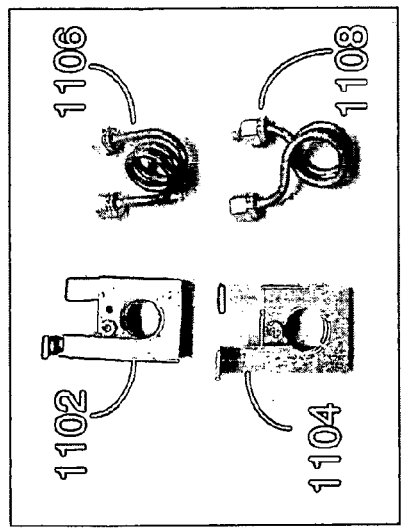
FIG. 23 shows an axial view of the induction devices with plate electrodes of FIG. 22 and a radial view of standard helical load coils of FIG. 22, in accordance with certain examples.

An induction device was constructed to generate a substantially symmetrical plasma discharge, as shown in FIG. 21. Referring to FIGS. 22 and 23, induction devices 1102 (three plates) and 1104 (two plates) were each used to generate a substantially symmetrical plasma discharge and conventional helical load coils 1106 (three turns) and 1108 (two turns) are shown for comparison purposes. The blocks that are used to mount the helical load coil to the oscillator also include existing hardware (screws) that hold the block to the faceplate. These screws were used to connect the induction device legs to the blocks after the helical coil was removed. No additional modifications were needed. With a conventional helical load coil, the discharge currents and resulting plasma temperatures tend to follow the helix of the load coil, which results in a non-uniform plasma discharge. This non-uniform discharge has many disadvantages including skewed ion trajectory, non-uniform heating of the sample, sample spilling around the outside of the plasma due to the non-flat bottom of the plasma, and less well defined regions of ionization. By using the induction devices disclosed herein instead of the wound copper tubing in helical load coils, it is possible to better control the temperature gradient in the plasma and provide a more symmetrical plasma. Additional tuning can be provided using the induction device disclosed herein by changing the spacing between plates of the induction device. For example it may be beneficial to stagger the spacing in between the plates of an induction device. If changing the spacing is attempted with a conventional coil by increasing the spacing between the load coil turns the plasma tends to become even more asymmetrical.

Figure 24:
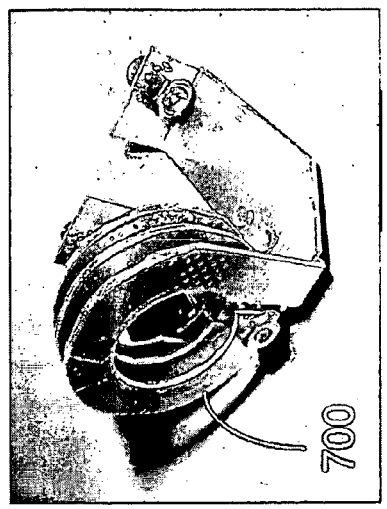
FIG. 24 is a 3-turn induction device, in accordance with certain examples.

It was found that use of the induction device disclosed herein improved sensitivities, especially in the low mass range (5-60 Atomic Mass Units (AMU)), lowered oxide ratios, and lowered working pressures. A symmetrical plasma, for example, also allows for running volatile samples without having the sample escape around the side of the plasma, provides a better defined ionization region, and removes the high background spike where the load coil peals off at the top of the plasma plume. FIG. 24 shows an exemplary plate induction device 700 that was tested in an Elan 6000 ICP mass spectrometer, available from PerkinElmer, Inc. Induction device 700 worked with both tube and solid state RF generators, and on both a ICP mass spectrometer and ICP-OES generators.

Example 3

Spacer Combinations

Various induction devices having different numbers of turns and different spacers were tested using ICP mass spectroscopy. The standard Elan generator uses a 3 turn load coil made out of 1/8" copper tubing and electrically connected to the generator using Swaglock fittings. When the induction devices were used, they were directly bolted to the existing electrodes in place of the Swaglock fittings. For each induction device, the unit (an ELAN 6000 commercially available from PerkinElmer, Inc.) was optimized and then data was gathered for different aspirated species including magnesium (Mg), rhodium (Rh), lead (Pb), cerium (Ce), cerium oxide (CeO), barium (Ba), barium+2 (Ba++), and background signal (BG 220). The data was normalized to the maximum sensitivity signal and plotted with the results shown in FIGS. 25-31. The various sensitivities were normalized to the maximum signal detected using a standard ELAN 6000 having a helical load coil (1/8 inch diameter copper tubing with 3 turns). The combination of induction devices that were tested were mixes of Standard 5 turn L2 inductor devices, a 4 turn L2 inductor and the 0.875 diameter plate induction device with different number of spacers between the plates. The term "L2 inductor," which is used in the abbreviations herein, represents part of the internal impedance matching coil, located inside the RF generator. The normal operating power (unless otherwise specified) was 1000 watts. Each spacer was a 632 brass washer. The combinations of induction devices that were tested are listed below. The abbreviations are referenced in FIGS. 25-31.

1. Standard Load coil with Standard 5 turn L2 inductor.
2. 1S5T—Plate induction device, one spacer between plates and standard 5 turn L2 inductor.
3. 1S4T—Plate induction device, one spacer between plates and 4 turn L2 inductor.
4. 1-2S4T—Plate induction device, one rear spacer, 2 front spacers and 4 turn L2 inductor.
5. 1-2S5T—Plate induction device, one rear spacer, 2 front spacers and 5 turn Standard L2 inductor.
6. 2S5T—Plate induction device, two spacers between plates and 5 turn Standard L2 inductor.
7. 2S4T—Plate induction device, two spacers between plates and 4 turn L2 inductor.
8. 3S4T—Plate induction device, three spacers between plates and 4 turn L2 inductor.
9. 3S5T—Plate induction device, three spacers between plates and 5 turn Standard L2 inductor.

When the data was plotted, data measured with the Plate induction device and Standard 5 turn L2 inductor had a double mountain indicating a pinch was present. The pinch refers to a secondary discharge between the plasma plume and the sampling interface. The pinch discharge can be eliminated by minimizing the plasma potential at the interface cone.

Figure 25:
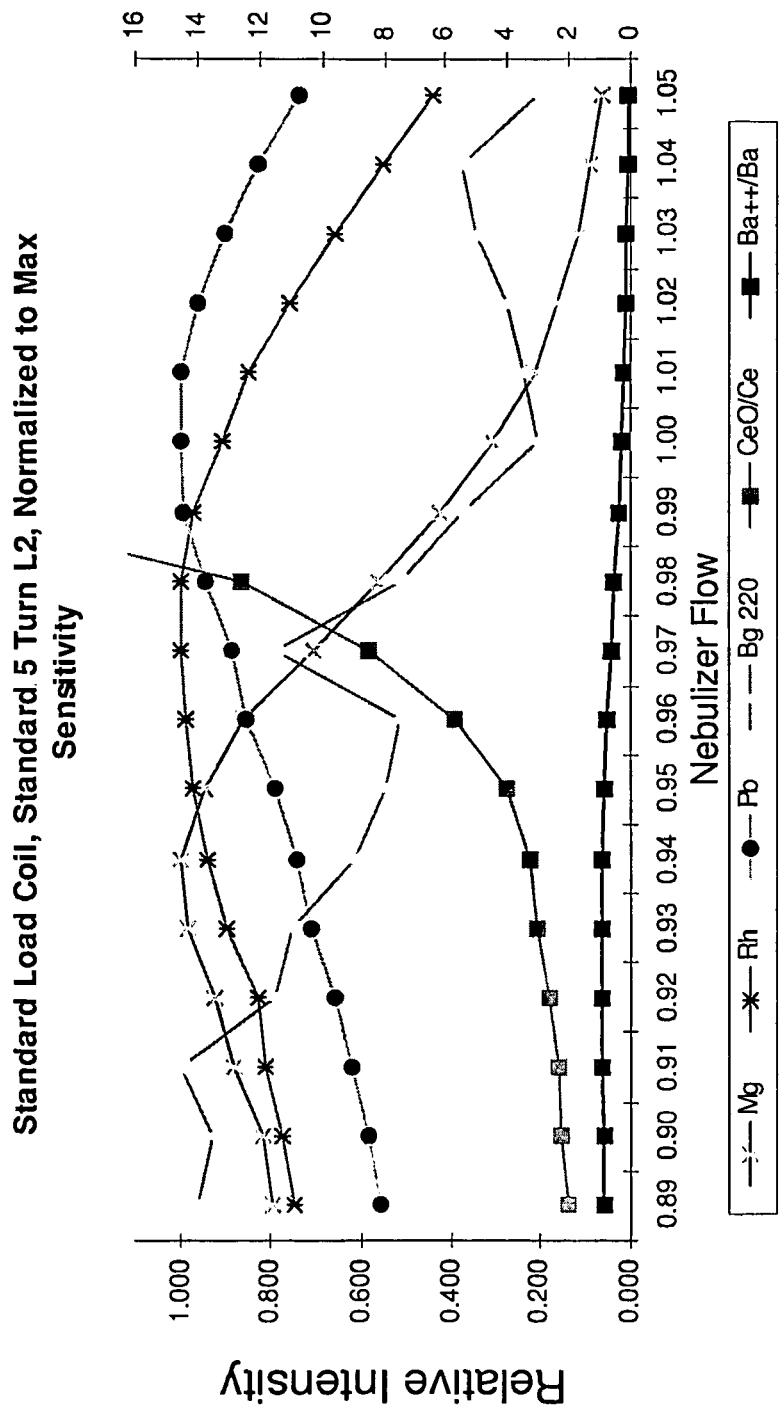
FIG. 25 is a graph showing the performance of a standard helical load coil for background and various metal species, in accordance with certain examples.

FIG. 25 is plot for each of the detected samples using a Standard ELAN 6000 mass spectrometer to which the all measurements were compared. The left axis represents normalized intensity, the x-axis represent nebulizer flow in L/min and the right axis represents either counts/second (for the BG 220 measurements) or percentage of oxides (for the CeO/Ce and Ba++/Ba measurements). The maximum sensitivity peaks of the different elements occur at different nebulizer flow rates. For sensitivity reasons, it is preferable for the maximum sensitivity of the elements to occur at a lower flow rate than the flow rate used to observe the maximum sensitivity of oxides, such as cerium oxide, as oxides tend to interfere with measurement of other species.

Figure 26:
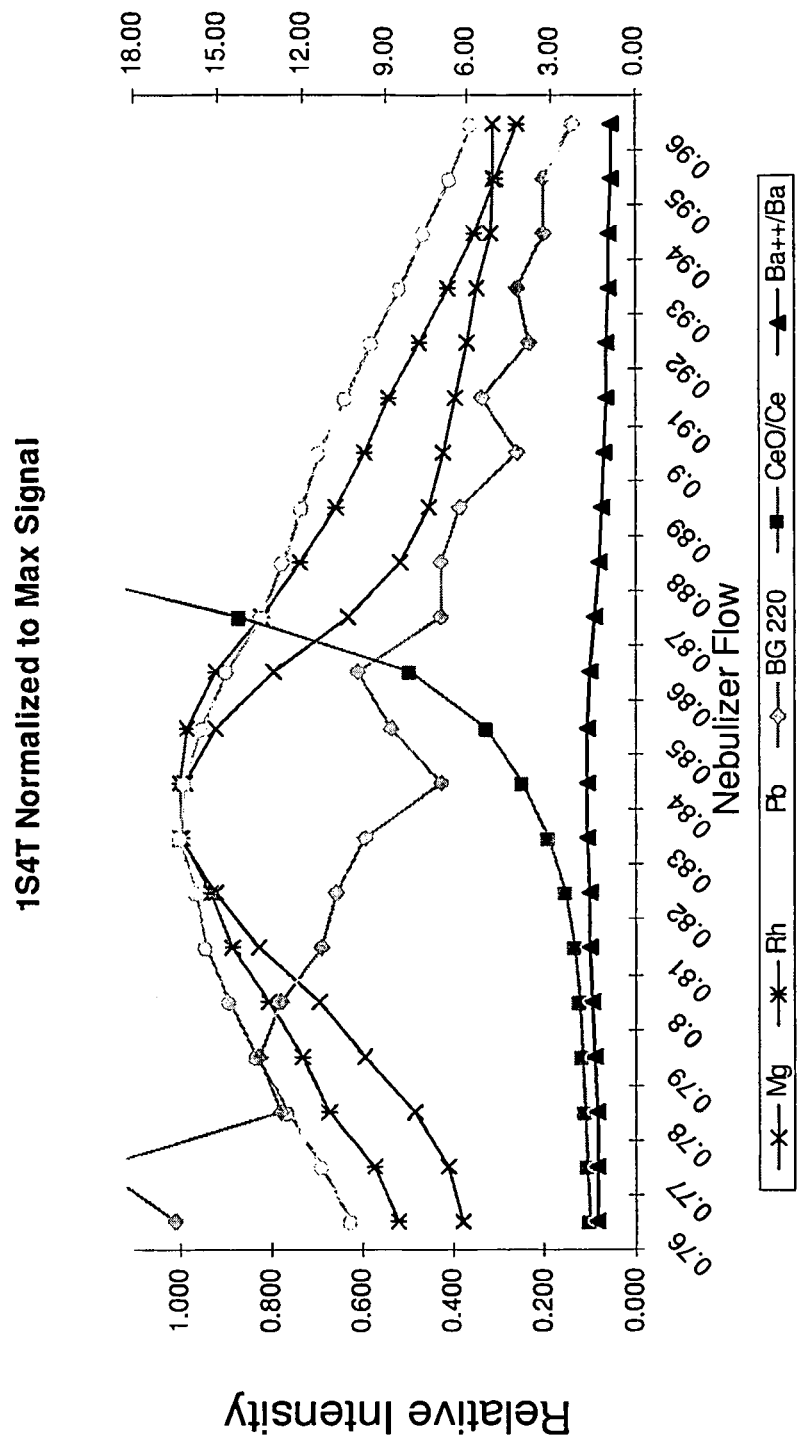
FIG. 26 is a graph showing the performance of a 1S4T induction device (1 spacer, 4 turns), normalized using the performance of the standard helical load coil, for background and various metal species, in accordance with certain examples.

Referring now to FIG. 26, the results from testing a 4 turn L2 internal impedance matching inductor and configuration (1S4T) are shown. Using the 1S4T device, the maximum sensitivity peak of the different elements (Mg, Rh, Pb) occurred at the same nebulizer flow (about 0.84). The single spacer gave highest mid mass sensitivity (mid mass typically refers to species having atomic mass units between 60-180 AMU, and high mass refers to species having atomic mass units from 180-238 AMU).

Figure 27:
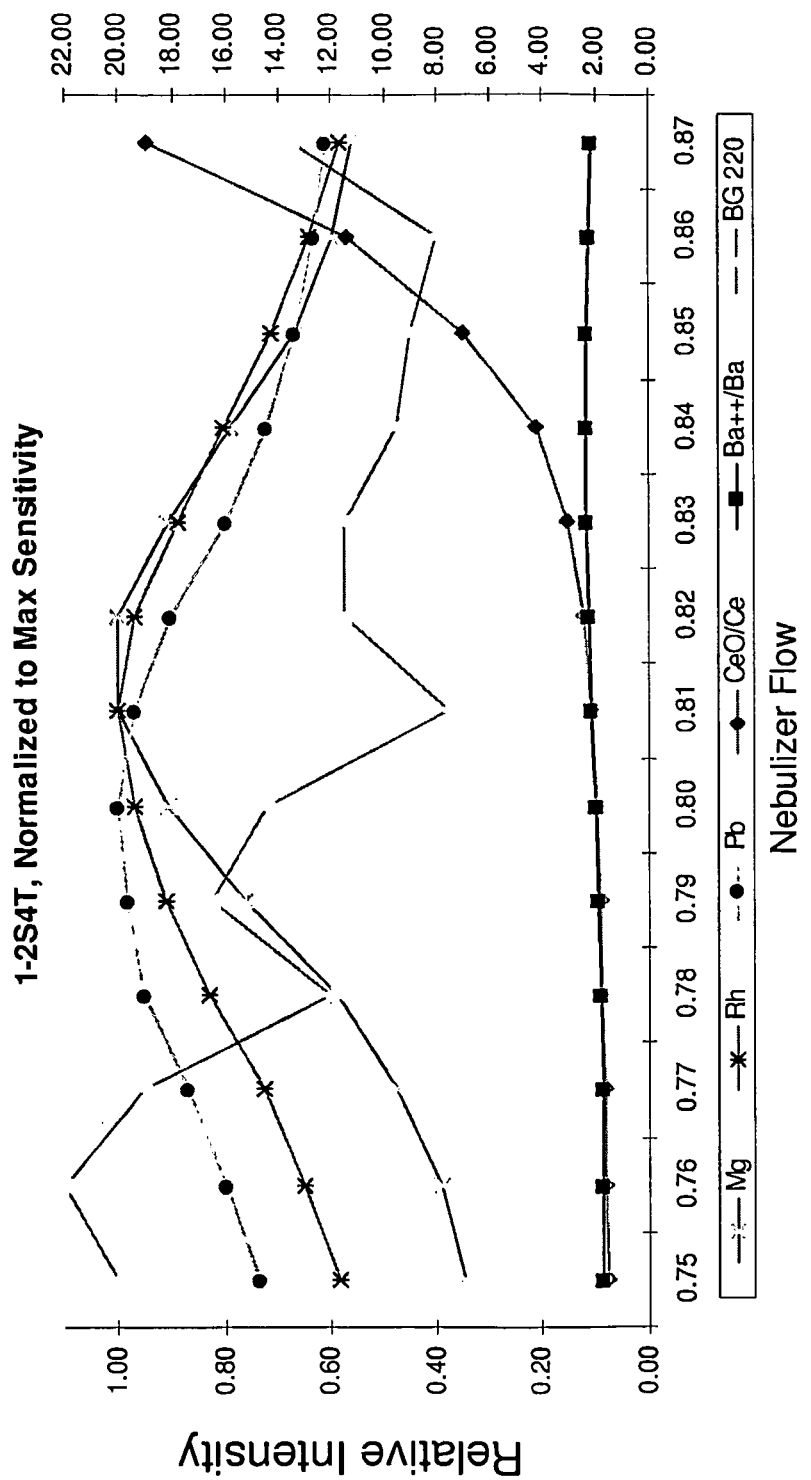
FIG. 27 is a graph showing the performance of a 1-2S4T induction device (2 spacers, 4 turns), normalized using the performance of a standard helical load coil, for background and various metal species, in accordance with certain examples.

Referring now to FIG. 27, the results from testing a double front single rear spacer 4 turn L2 inductor (1-2S4T) are shown. Using the 1-2S4T device it was possible to separate the magnesium, rhodium, and lead signals away from the top of oxide mountain (TOM) observed with Ce/CeO.

Figure 28:
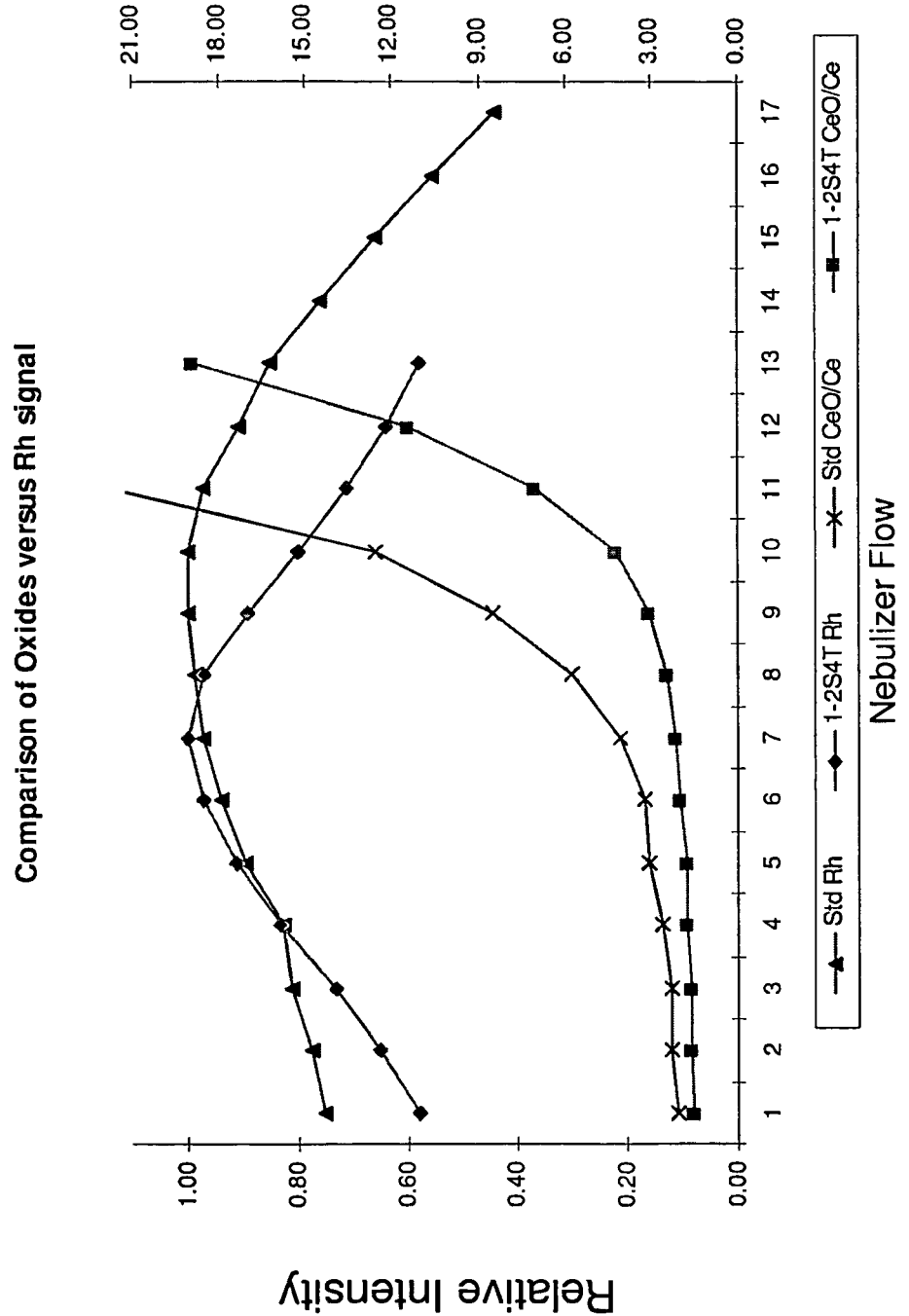
FIG. 28 is a graph comparing the performance of various induction devices for oxide and rhodium samples, in accordance with certain examples.

Referring now to FIG. 28, various load coils were tested for rhodium sensitivity as compared to cerium oxide/cerium signal. Tested devices included the standard helical load coil and a plate induction device having one rear spacer, 2 front spacers and 4 turn L2 inductor (1-2S4T). Using the 1-2S4T device, the maximum sensitivity peak of the rhodium was shifted to lower flow rates and away from the maximum sensitivity peak of the cerium oxide/cerium, indicating the 1-2S4T device provided better rhodium sensitivity than the standard coil.

Figure 29:
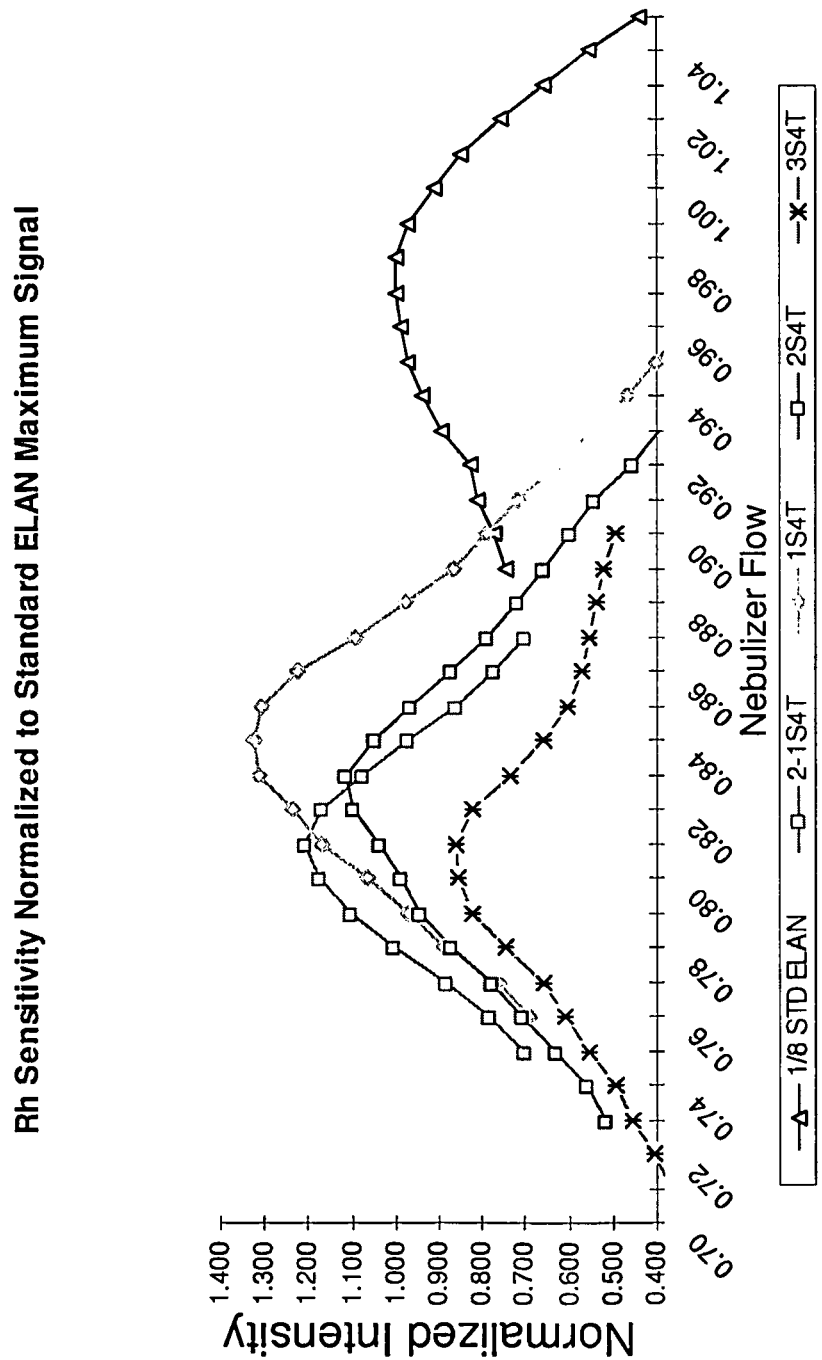
FIG. 29 is graph comparing the rhodium signal from various induction devices, in accordance with certain examples.

Referring now to FIG. 29, the rhodium signal was normalized to the maximum standard signal from the ELAN 6000. Use of the 1S4T device provided a 30% signal increase as compared to the standard helical load coil. Use of the 1-2S4T device separated the oxide mountain observed with the standard coil.

Figure 30:
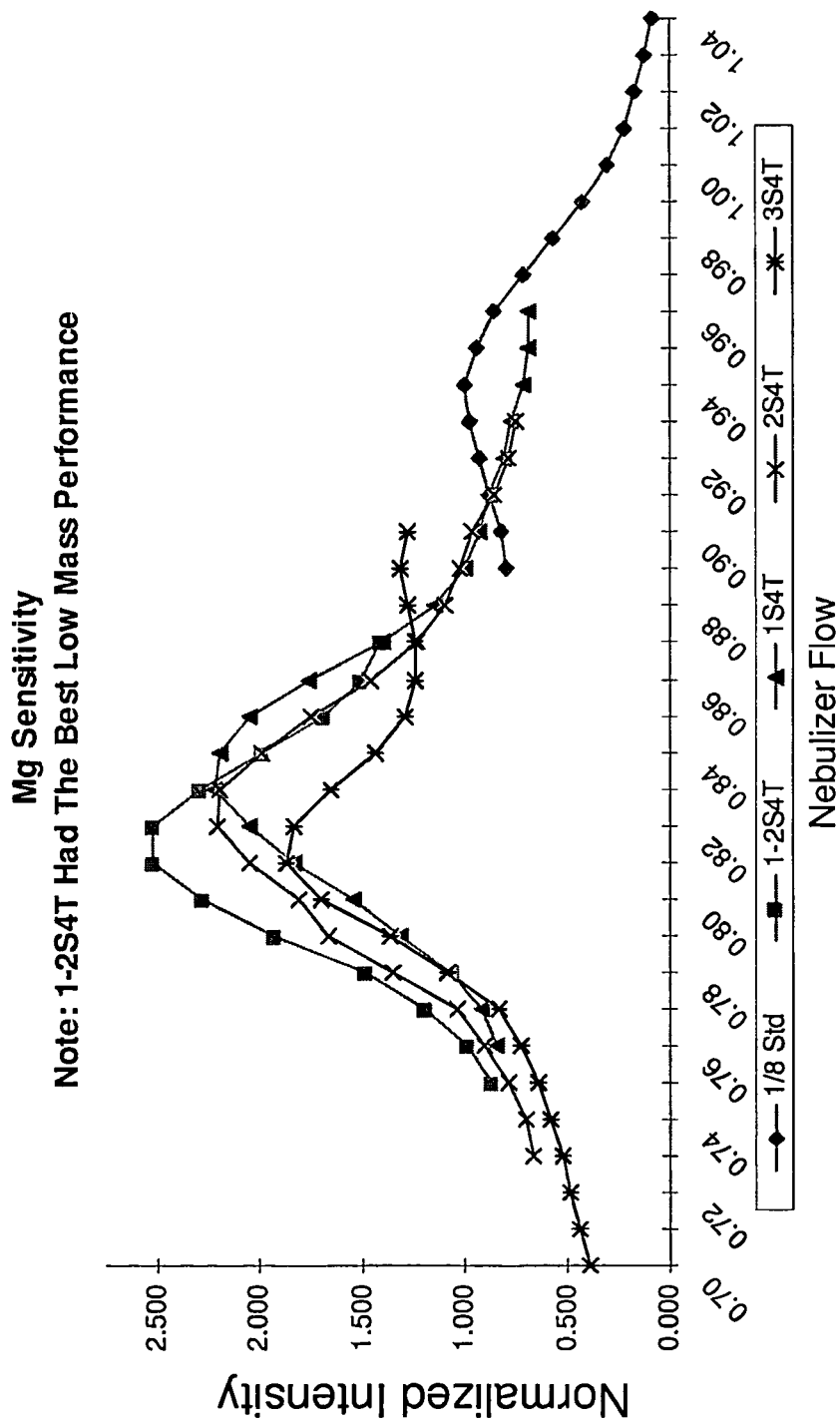
FIG. 30 is a graph comparing the performance of various load coils for a magnesium sample, in accordance with certain examples.

Referring now to FIG. 30, magnesium was used to measure the performance of the various devices. The 1-2S4T device exhibited the best low mass performance of all the devices tested.

Figure 31:
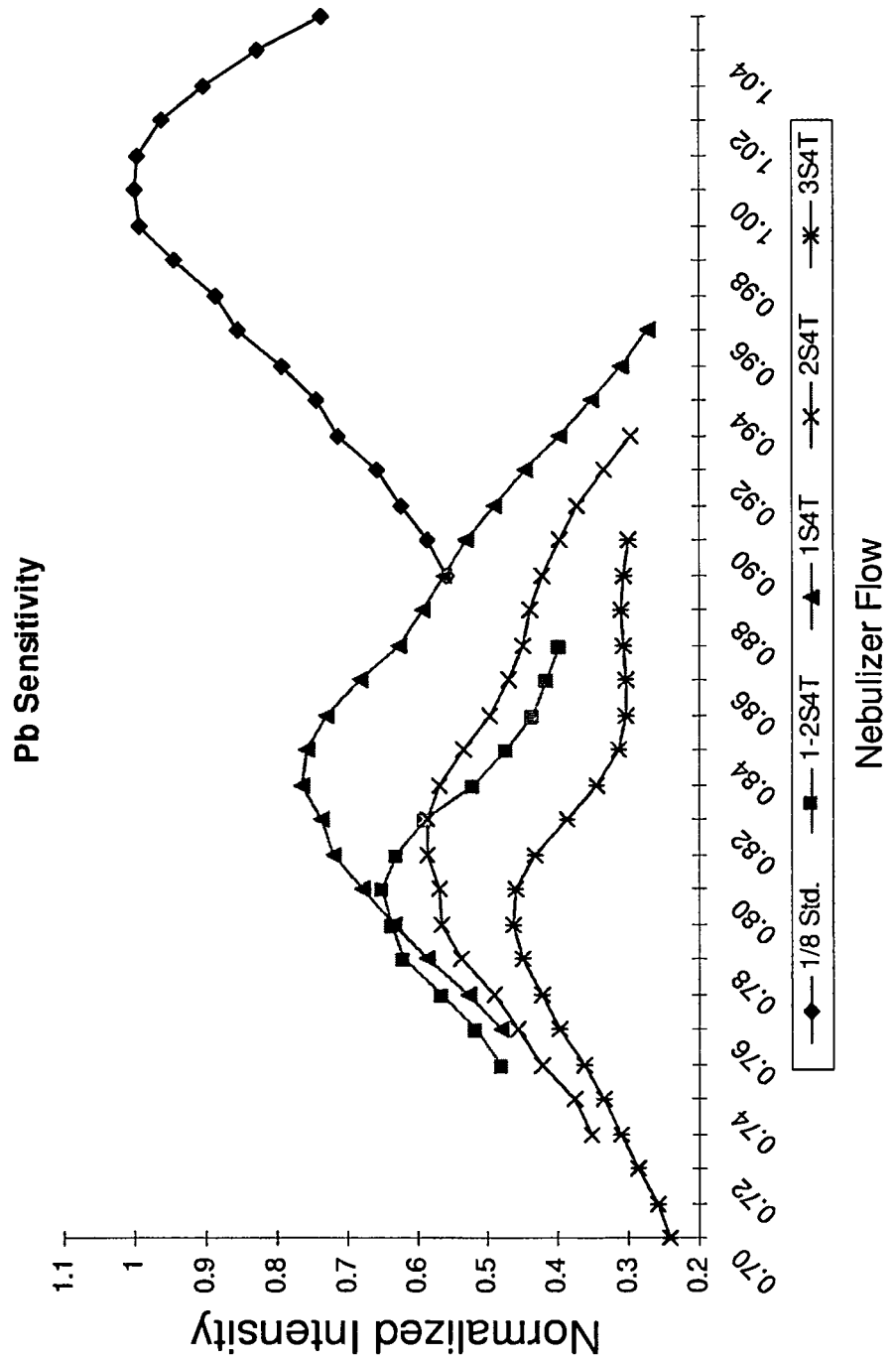
FIG. 31 is graph comparing the high mass performance of various load coils, in accordance with certain examples.

Referring now to FIG. 31, lead was used to measure the high mass performance of the various devices. The plate induction devices all gave poorer high mass performance than the standard ELAN 6000 at nebulizer flow rates greater than about 0.96. At lower nebulizer flow rates, however, the plate induction devices all give better high mass performance than the standard ELAN 6000, which may allow detection of high mass species using reduced amounts of sample.

Example 4

Optical Emission Detection Limits Using Plate Induction Coils

An optical emission spectrometer (Optima 3000 obtained from PerkinElmer, Inc.) was fitted with either a helical load coil or a plate induction device to measure the detection limits for arsenic (As), cadmium (Cd), chromium (Cr), manganese (Mn), lead (Pb) and selenium (Se). The helical load coil was the standard 3/16" diameter copper coil. The plate induction device included two circular electrodes each having an aperture for receiving a torch. For comparison purposes only, the detection limits using the helical load coil and the plate induction device are shown in Table I below.

TABLE I

| Element | Emission Wavelength (nm) | Detection Limit (ppb) Helical Load Coil | Detection Limit (ppb) Plate Induction Device |
|---|---|---|---|
| Arsenic | 197 | 34 | 10 |
| Cadmium | 214 | 0.8 | 0.3 |
| Chromium | 205 | 1.7 | 0.6 |
| Manganese | 257 | 0.15 | 0.1 |
| Lead | 220 | 8 | 4 |
| Selenium | 196 | 26 | 14 |

While detection limits on newer instruments may be better than those listed in Table I above, a relative comparison of the detection limits reveals that the detection limits using the plate induction device were consistently lower than the detection limits obtained using the helical load coil.

When introducing elements of the examples disclosed herein, the articles "a," "an," "the" and "said" are intended to mean that there are one or more of the elements. The terms "comprising," "including" and "having" are intended to be open ended and mean that there may be additional elements other than the listed elements. It will be recognized by the person of ordinary skill in the art, given the benefit of this disclosure, that various components of the examples can be interchanged or substituted with various components in other examples. Should the meaning of the terms of any of the patents, patent applications or publications incorporated herein by reference conflict with the meaning of the terms used in this disclosure, the meaning of the terms in this disclosure are intended to be controlling.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A device for generating a plasma in a torch having a longitudinal axis along which a flow of gas is introduced during operation of the torch and having a radial plane substantially perpendicular to the longitudinal axis of the torch, the device comprising a first electrode, a second electrode and a third electrode each configured to couple to a power source and constructed and arranged to provide a loop current along the radial plane of the torch, in which spacing between the first electrode and the second electrode and spacing between the second electrode and the third electrode is substantially the same.

2. The device of claim, in which each of the first, second and third electrodes each comprises a plate comprising a symmetrical inner cross-section.

3. The device of claim 2, in which the symmetrical inner cross-section is circular.

4. The device of claim, further comprising at least one spacer separating the first electrode and the second electrode.

5. The device of claim 1, in which each of the first electrode, the second electrode and the third electrode is configured to sustain a substantially symmetrical plasma in the torch.

6. The device of claim 1, further comprising a radio frequency source in electrical communication with the first electrode, the second electrode and the third electrode.

7. The device of claim 6, in which the radio frequency source is configured to provide radio frequencies of about 1 MHz to about 1000 MHz at a power of about 10 Watts to about 10,000 Watts.

8. The device of claim 6, further comprising a second radio frequency source in electrical communication with the second electrode.

9. The device of claim, further comprising a radio frequency source in electrical communication with the first electrode, the second electrode and the third electrode.

10. The device of claim 9, in which the radio frequency source is configured to provide radio frequency energy of about 1 MHz to about 1,000 MHz at a power of about 10 Watts to about 10,000 Watts.

11. The device of claim, further comprising a grounding plate in electrical communication with the first electrode, the second electrode, and the third electrode.

12. The device of claim 11, in which the first electrode, the second electrode, the third electrode and the grounding plate are configured for use in an inductively coupled plasma optical emission spectrometer.

13. The device of claim 11, in which the first electrode, the second electrode, the third electrode and the grounding plate are configured for use in an inductively coupled plasma atomic absorption spectrometer.

14. The device of claim 11, in which the first electrode, the second electrode, the third electrode and the grounding plate are configured for use in an inductively coupled plasma mass spectrometer.

* * * * *